US011092698B2

(12) United States Patent
Tanaka et al.

(10) Patent No.: US 11,092,698 B2
(45) Date of Patent: Aug. 17, 2021

(54) RADIATION IMAGING SYSTEM, IMAGING APPARATUS, CONTROL APPARATUS, AND METHODS OF CONTROLLING THE SAME

(71) Applicant: CANON KABUSHIKI KAISHA, Tokyo (JP)

(72) Inventors: Hikaru Tanaka, Kawasaki (JP); Yuichi Nishii, Kawasaki (JP); Kenta Endoh, Tokyo (JP); Tomohiro Kawanishi, Tachikawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 64 days.

(21) Appl. No.: 16/381,608

(22) Filed: Apr. 11, 2019

(65) Prior Publication Data

US 2019/0235093 A1 Aug. 1, 2019

Related U.S. Application Data

(63) Continuation of application No. PCT/JP2017/035502, filed on Sep. 29, 2017.

(30) Foreign Application Priority Data

Oct. 14, 2016 (JP) .............................. JP2016-203038
Oct. 14, 2016 (JP) .............................. JP2016-203041
Mar. 15, 2017 (JP) .............................. JP2017-050291

(51) Int. Cl.
*G01T 1/20* (2006.01)
*A61B 6/00* (2006.01)
*H04N 5/32* (2006.01)

(52) U.S. Cl.
CPC ................. *G01T 1/20* (2013.01); *A61B 6/00* (2013.01); *A61B 6/563* (2013.01); *A61B 6/566* (2013.01); *H04N 5/32* (2013.01); *A61B 6/4233* (2013.01)

(58) Field of Classification Search
CPC .............. G01T 1/20; A61B 6/00; A61B 6/563
See application file for complete search history.

(56) References Cited

U.S. PATENT DOCUMENTS

2012/0130238 A1\* 5/2012 Muraoka ................ G16H 30/40
600/436
2013/0229280 A1 9/2013 Nishii
(Continued)

FOREIGN PATENT DOCUMENTS

JP 2011177348 A 9/2011
JP 2013090986 A 5/2013
(Continued)

OTHER PUBLICATIONS

Japanese Office Action dated Aug. 21, 2020, for Corresponding Japanese Application No. 2016203041.

*Primary Examiner* — Hugh Maupin
(74) *Attorney, Agent, or Firm* — Carter, DeLuca & Farrell LLP

(57) ABSTRACT

A radiation imaging system comprises a plurality of imaging apparatuses configured to generate images based on radiation emitted from a radiation generator, and a control apparatus configured to communicate with the plurality of imaging apparatuses. Each of the plurality of imaging apparatuses generates imaging information with a smaller data size than an image obtained by an imaging operation based on the image. The control apparatus acquires the imaging information from each of the plurality of imaging apparatuses, and selects, from the plurality of imaging apparatuses based on the imaging information, an imaging apparatus from which an image obtained by an imaging operation is acquired.

25 Claims, 26 Drawing Sheets

(56) References Cited

U.S. PATENT DOCUMENTS

2013/0232361 A1   9/2013  Nishii
2016/0081642 A1*  3/2016  Okusu .................. G06F 3/0482
                                                        378/62

FOREIGN PATENT DOCUMENTS

| JP | 5577114 B    | 8/2014 |
| JP | 2016000369 A | 1/2016 |
| JP | 2016140510 A | 8/2016 |

* cited by examiner

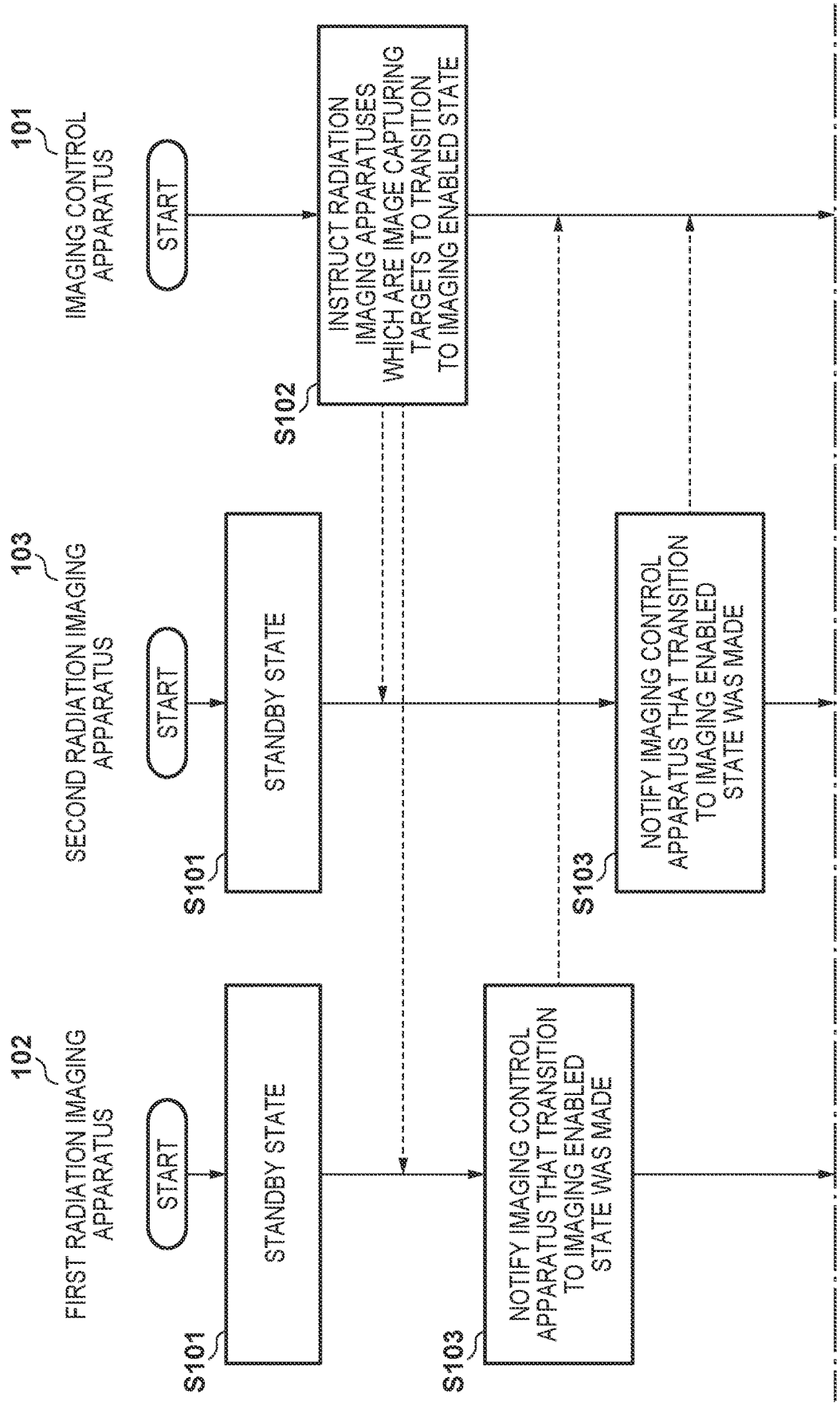

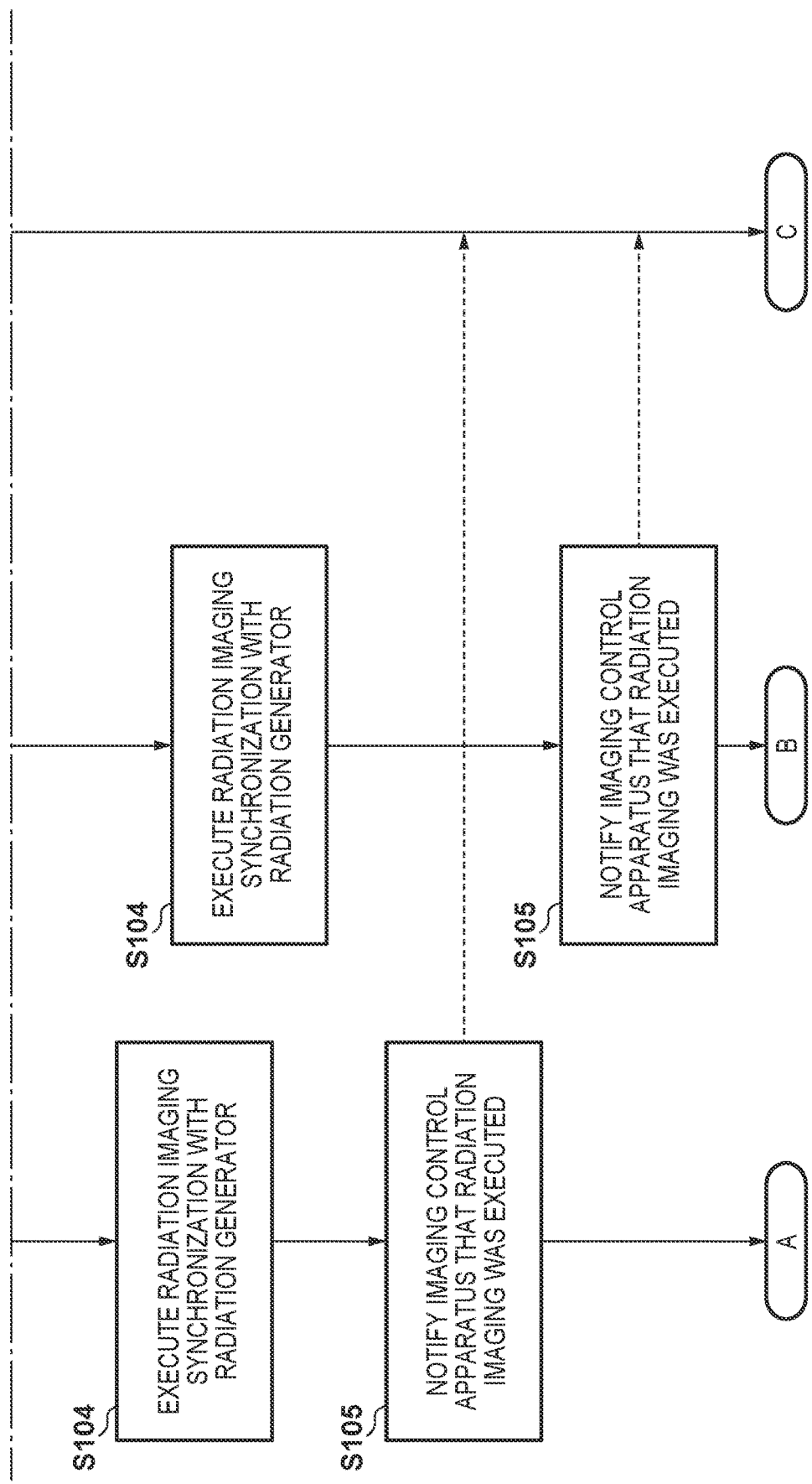

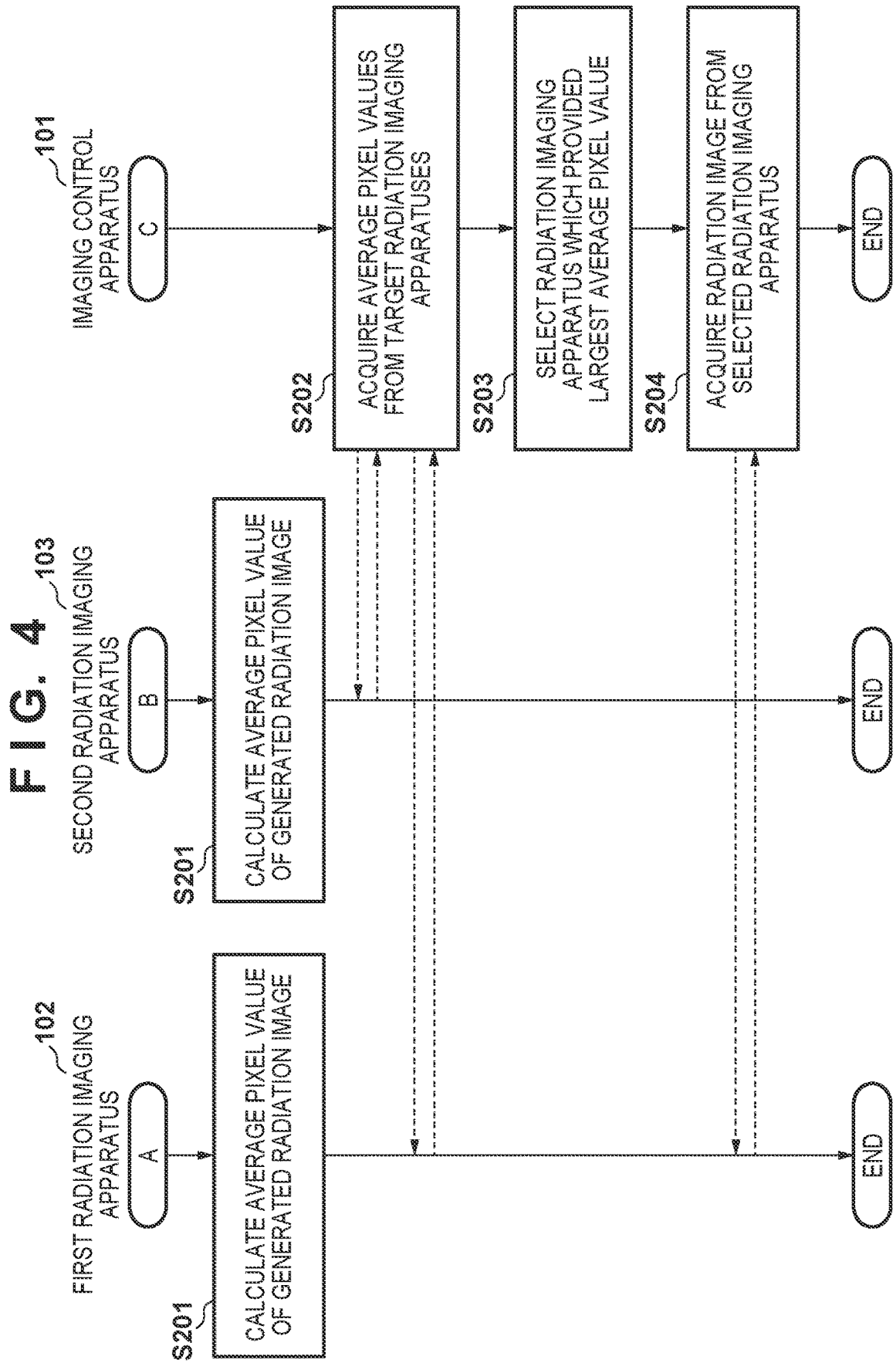

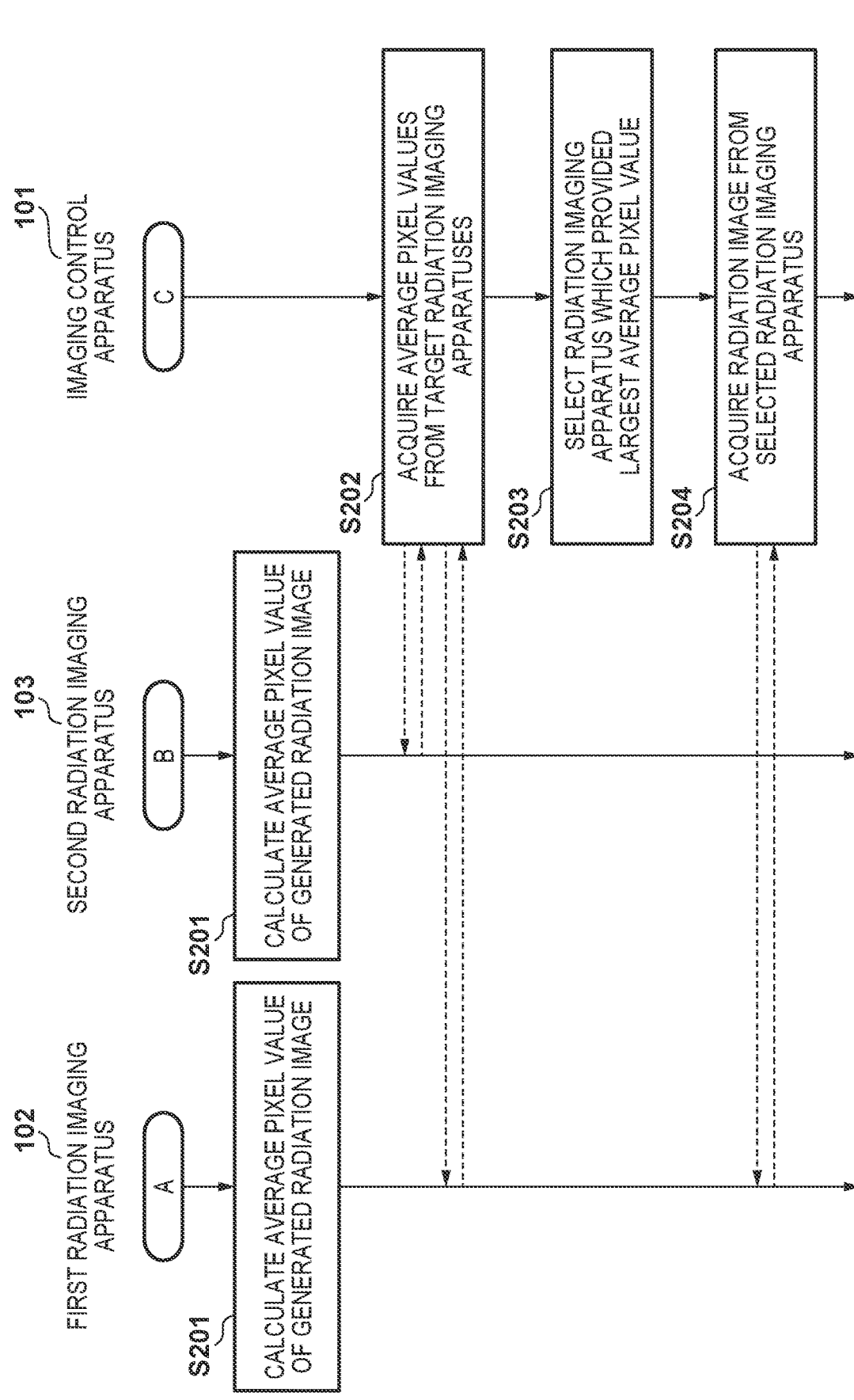

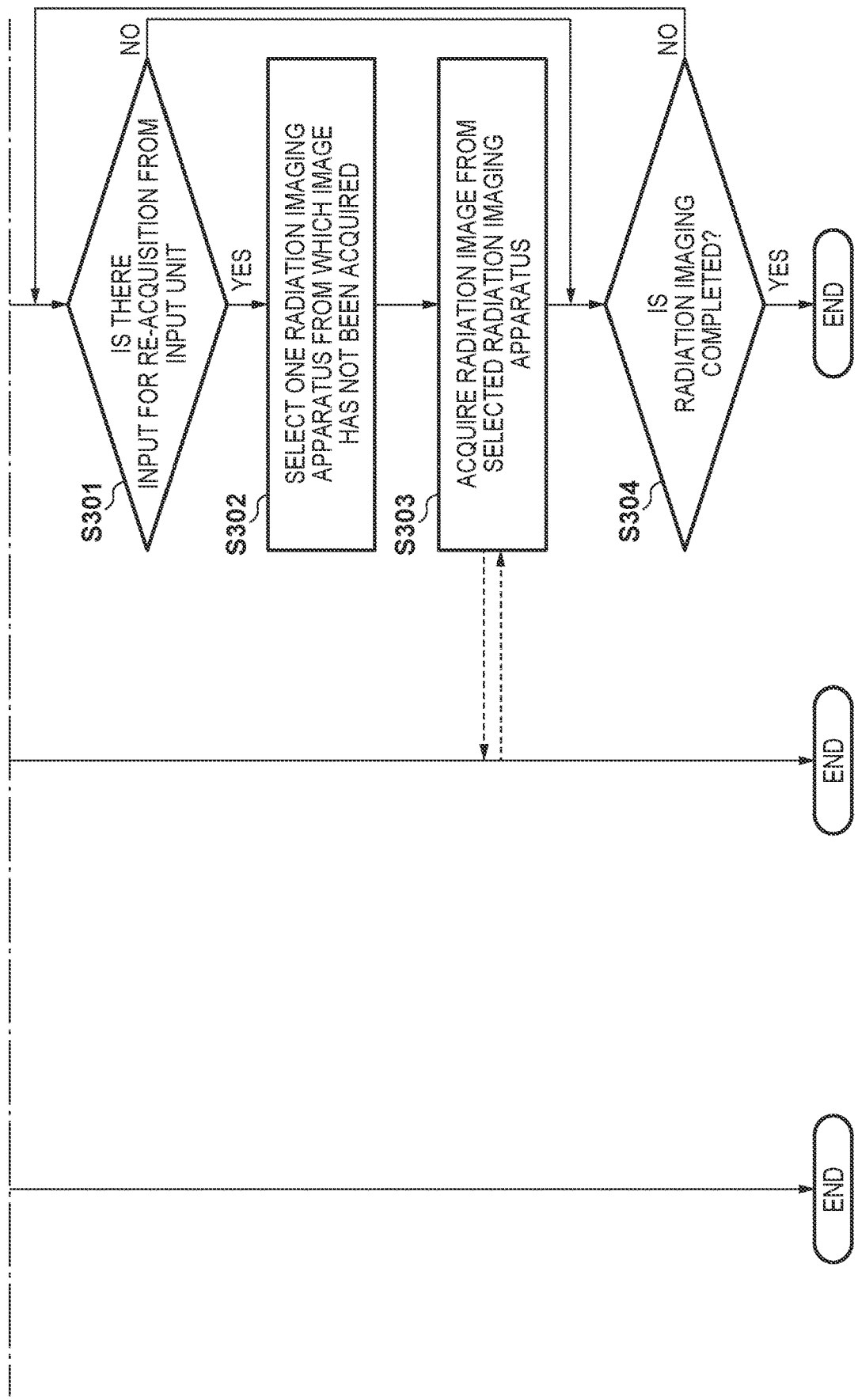

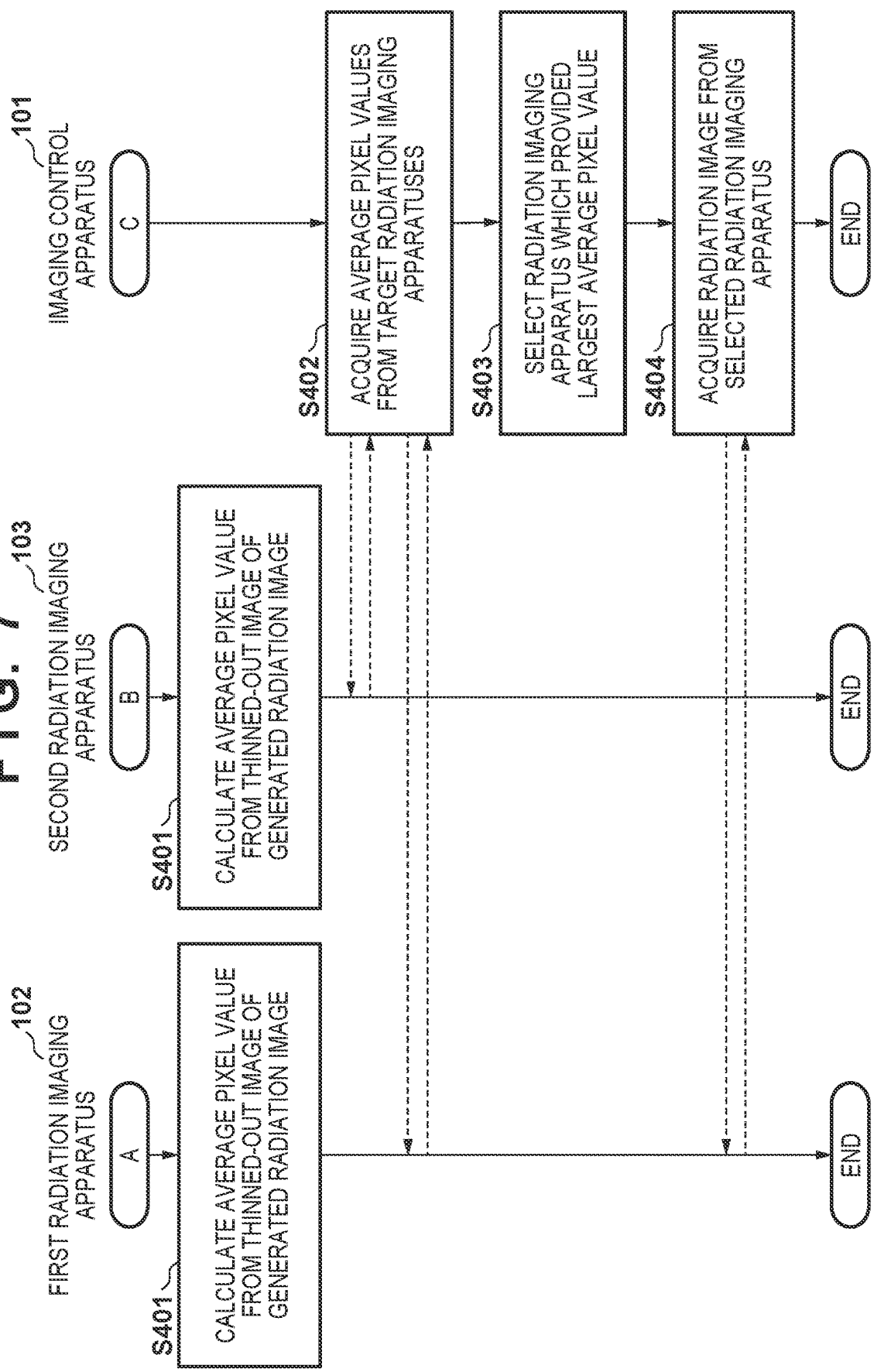

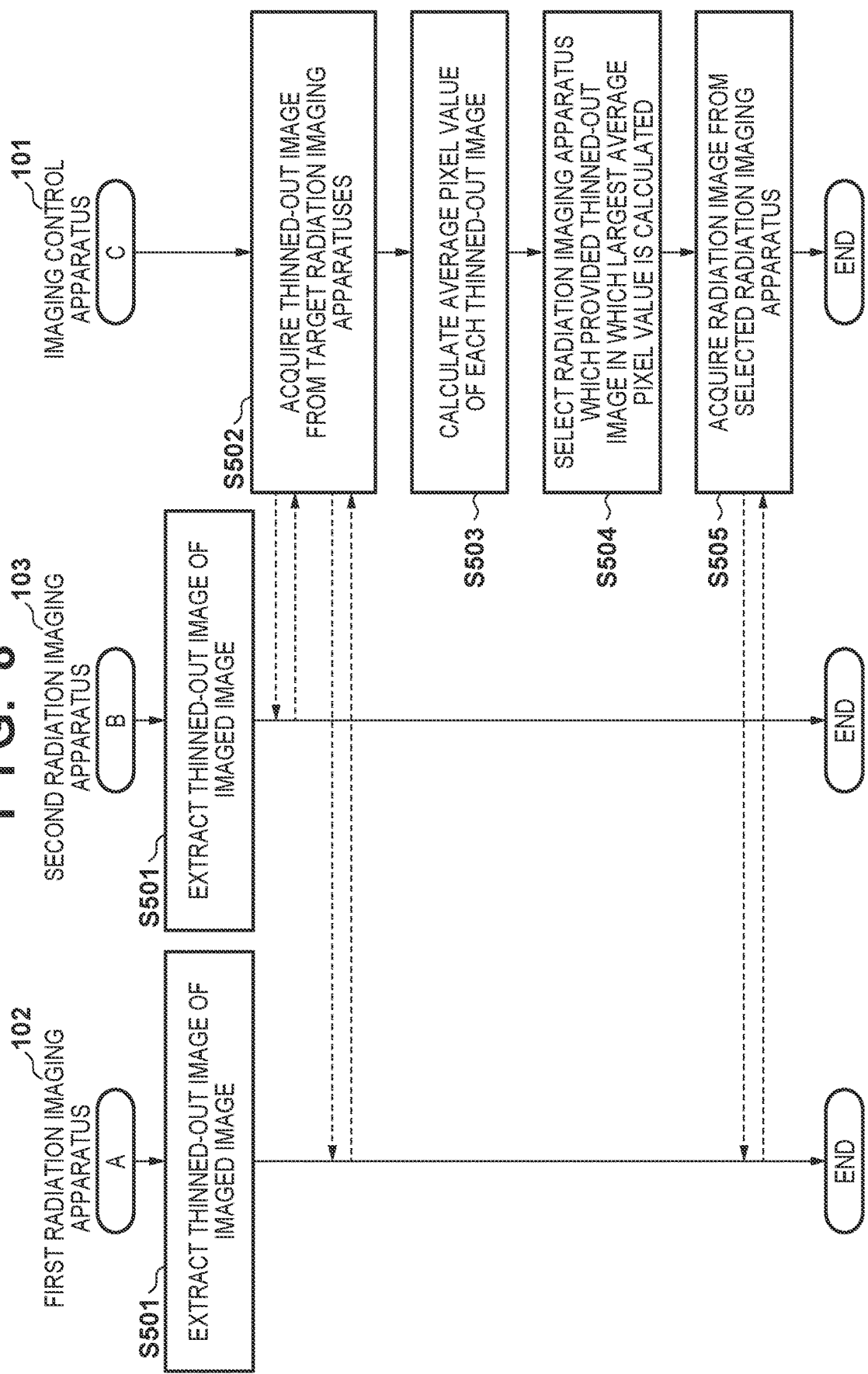

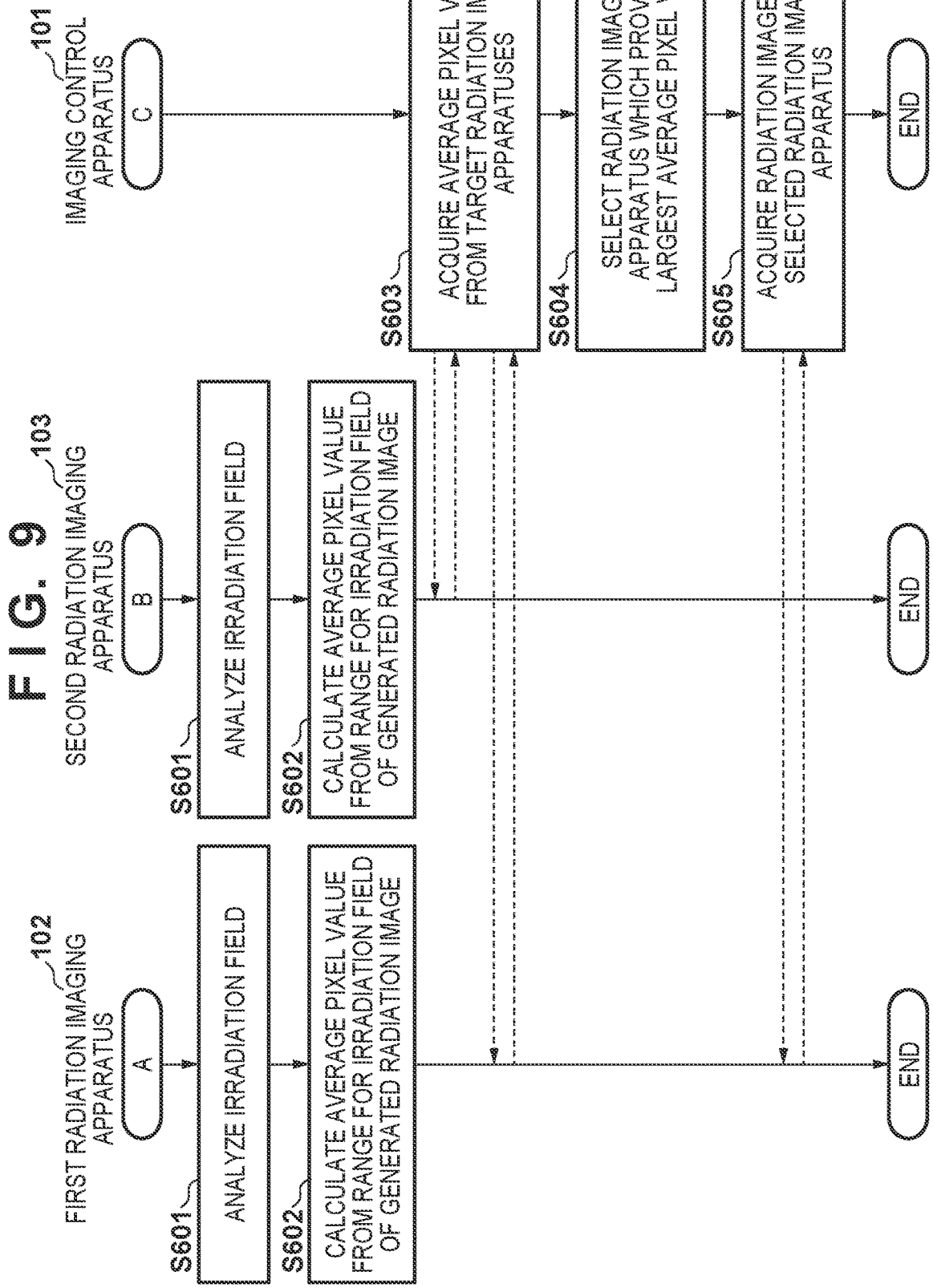

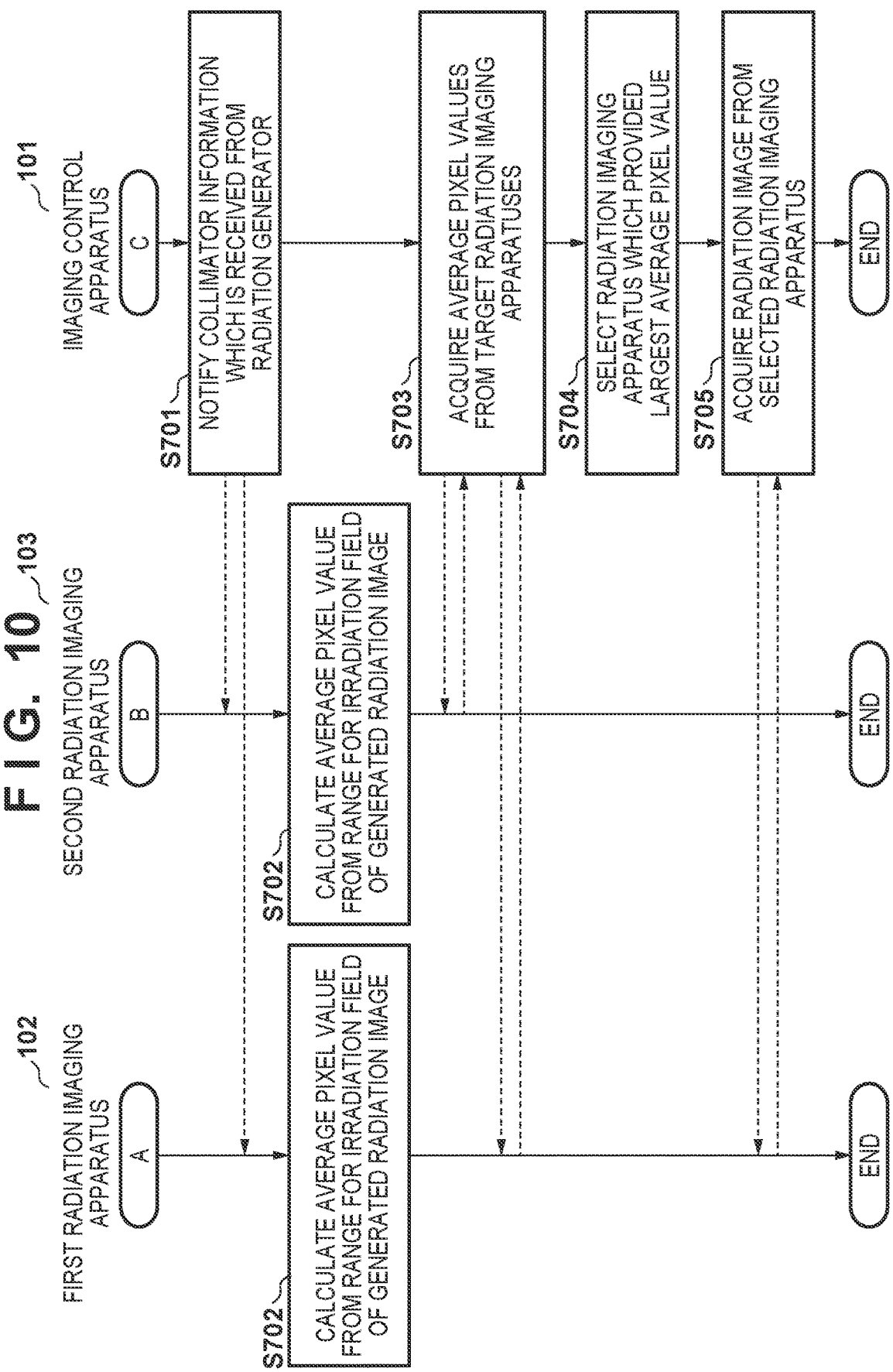

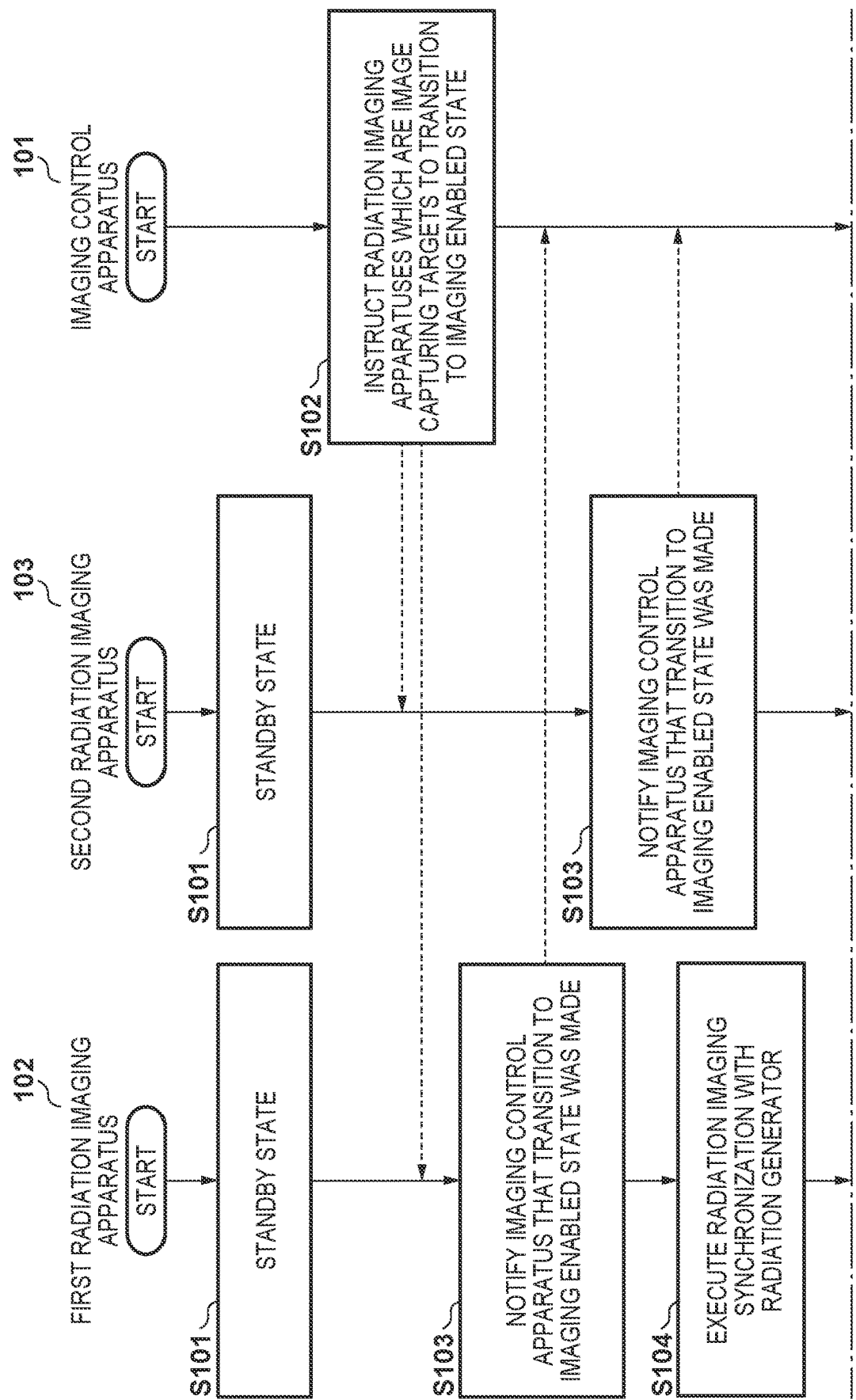

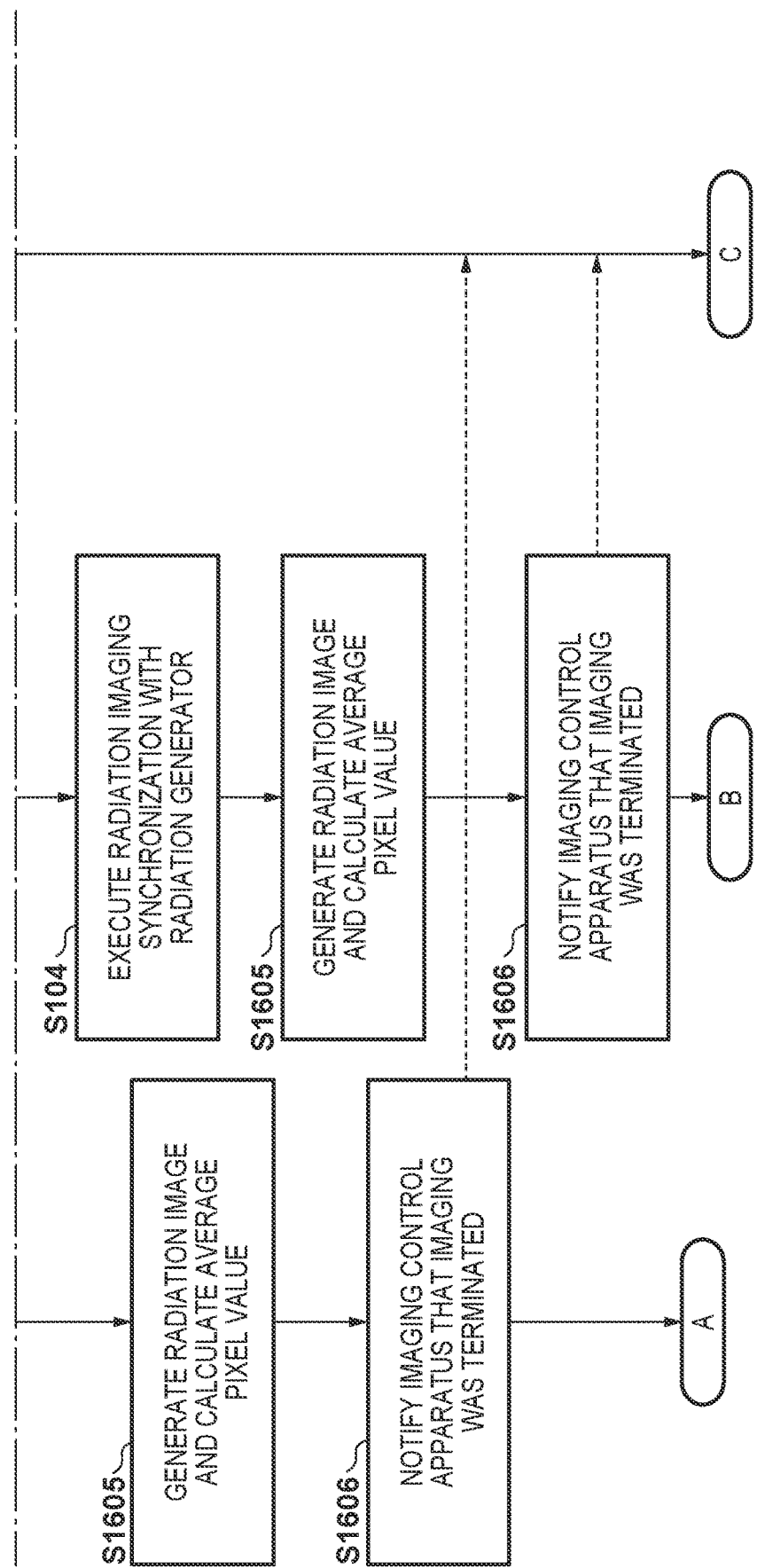

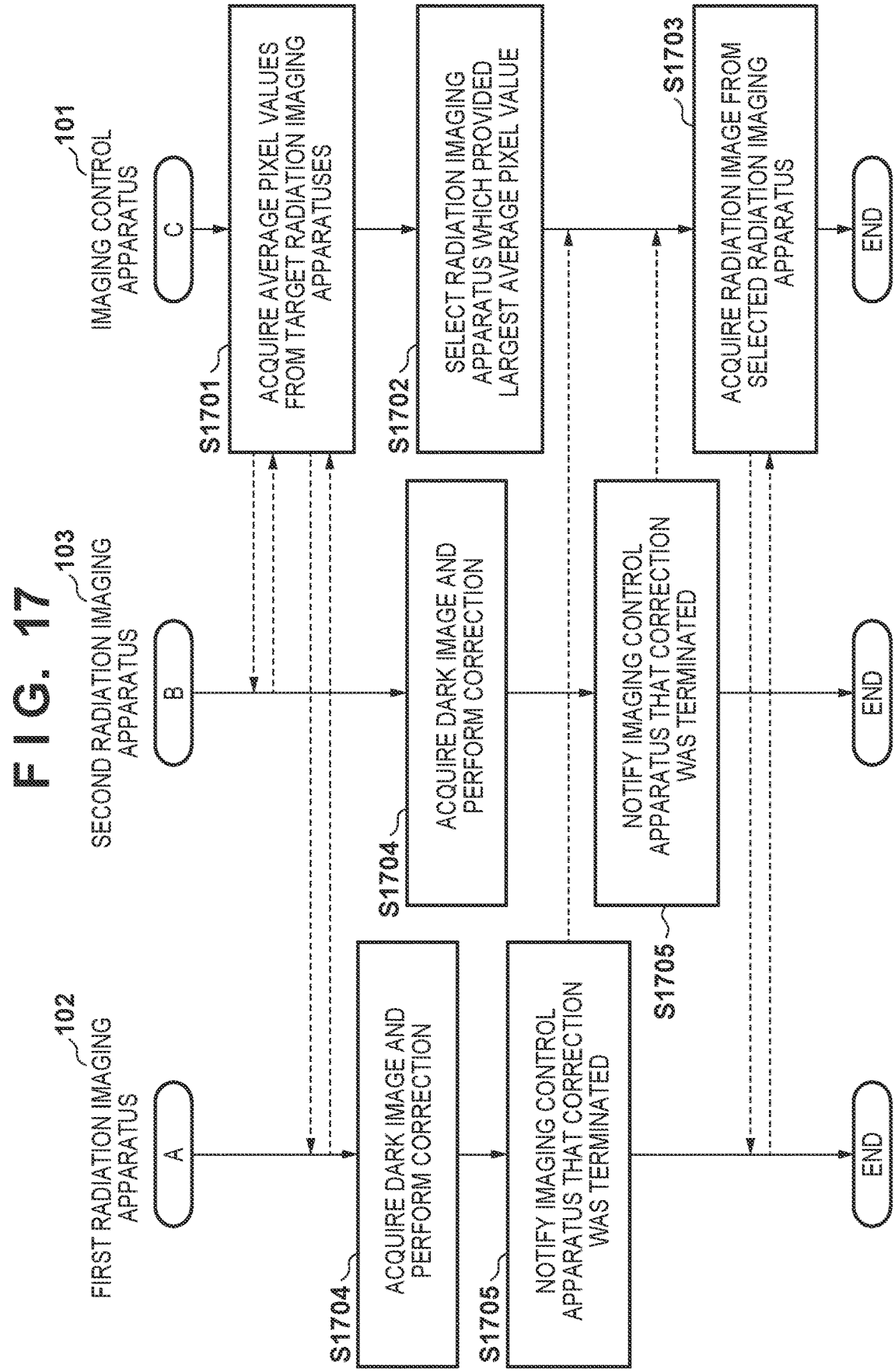

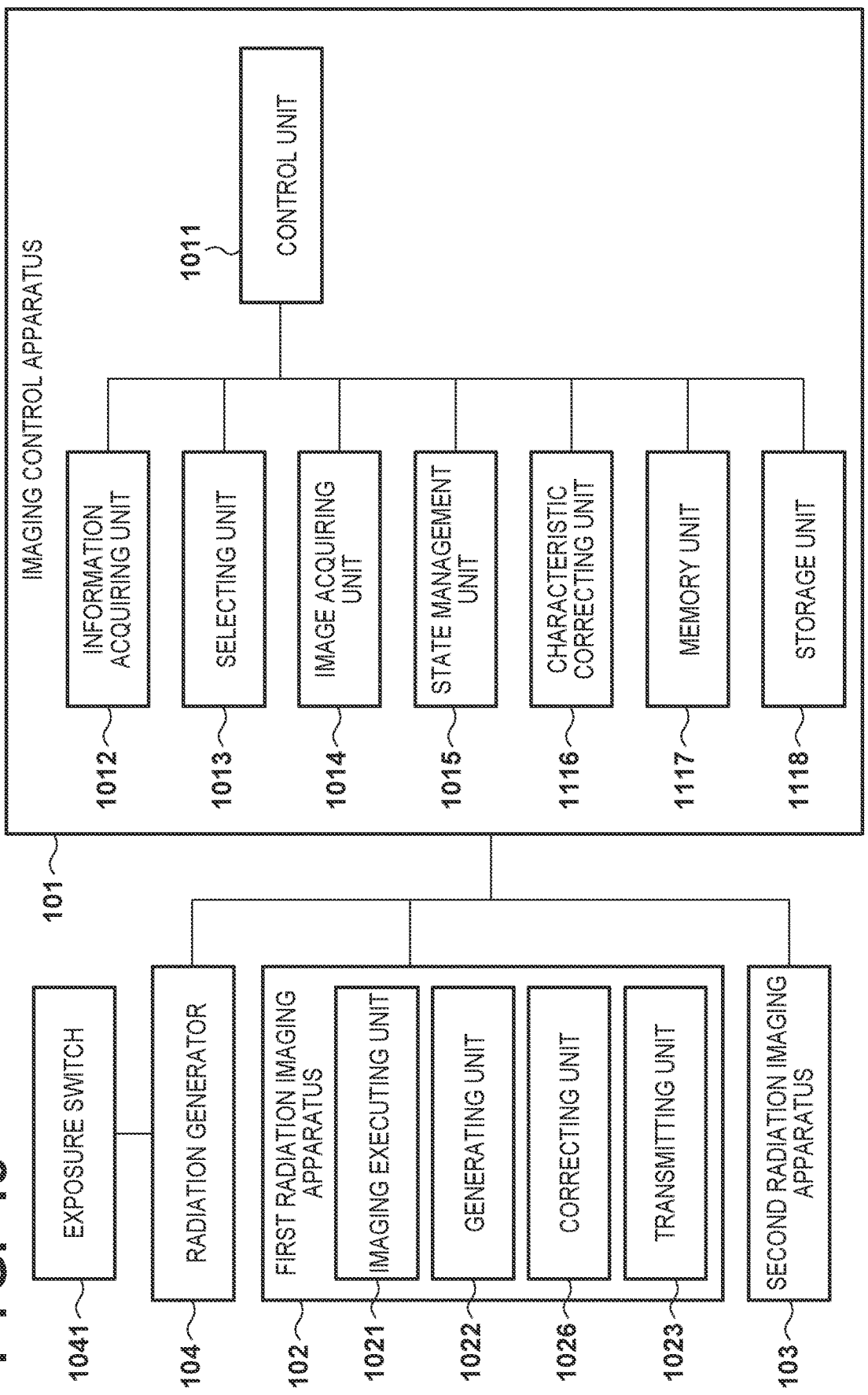

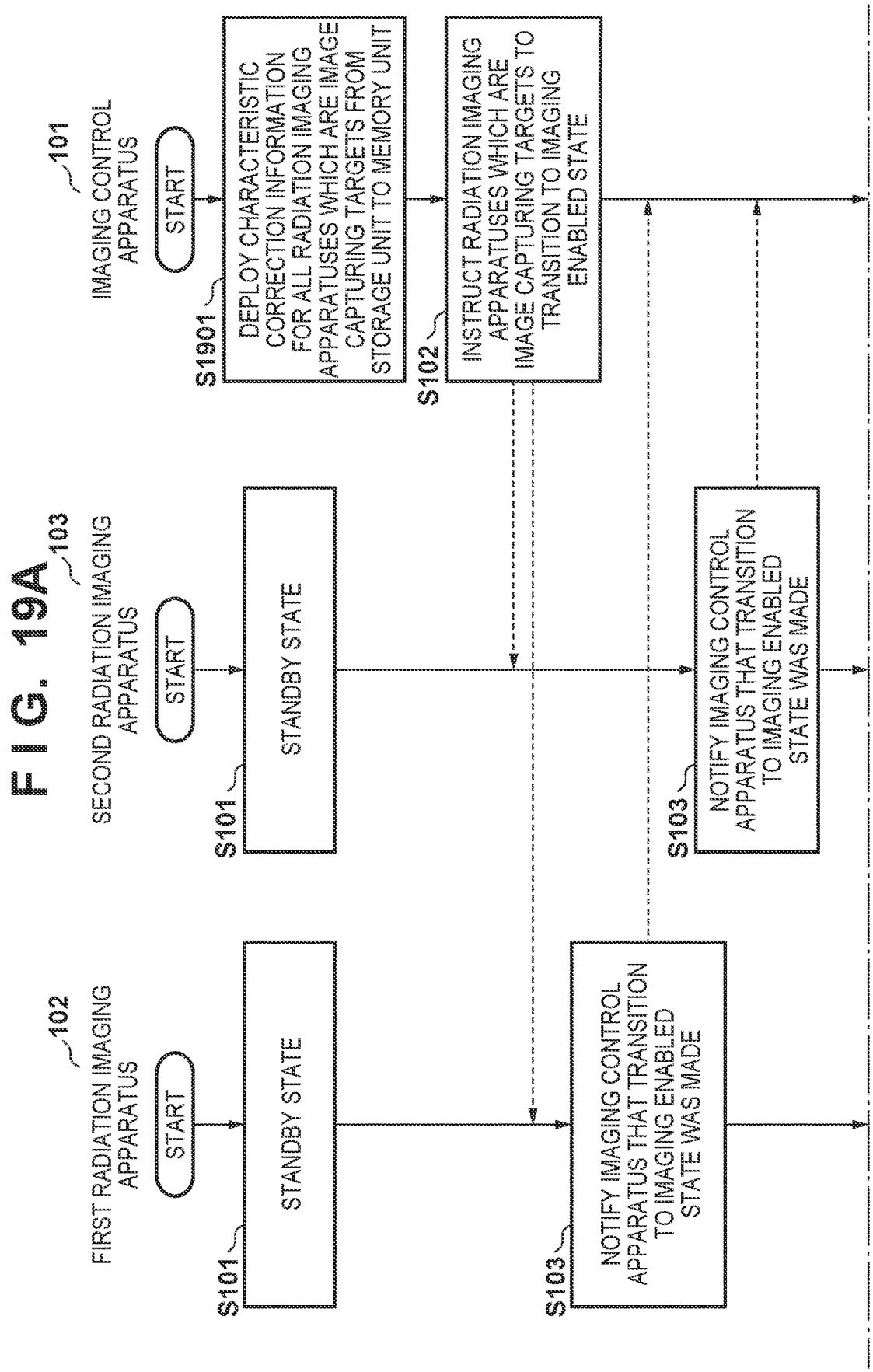

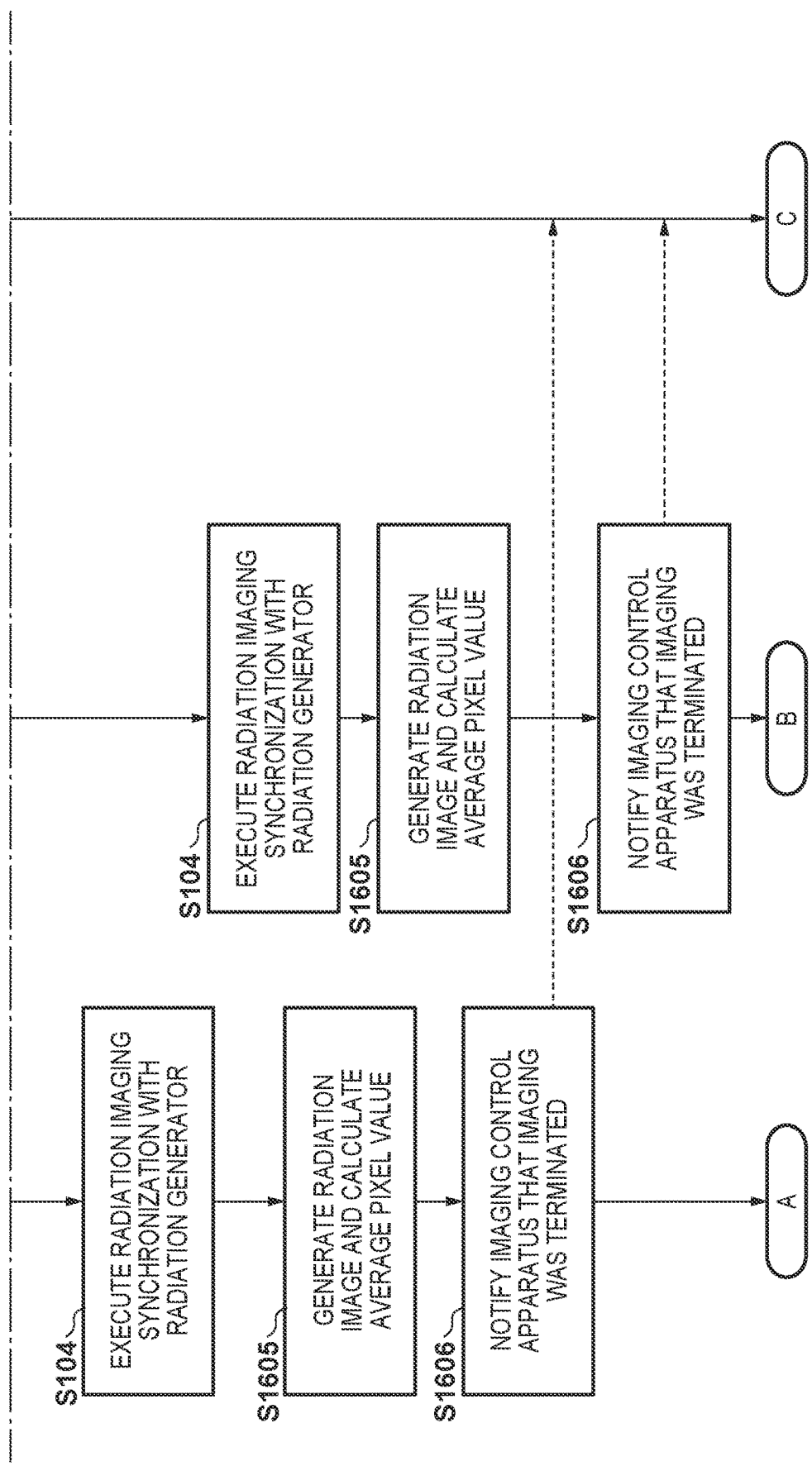

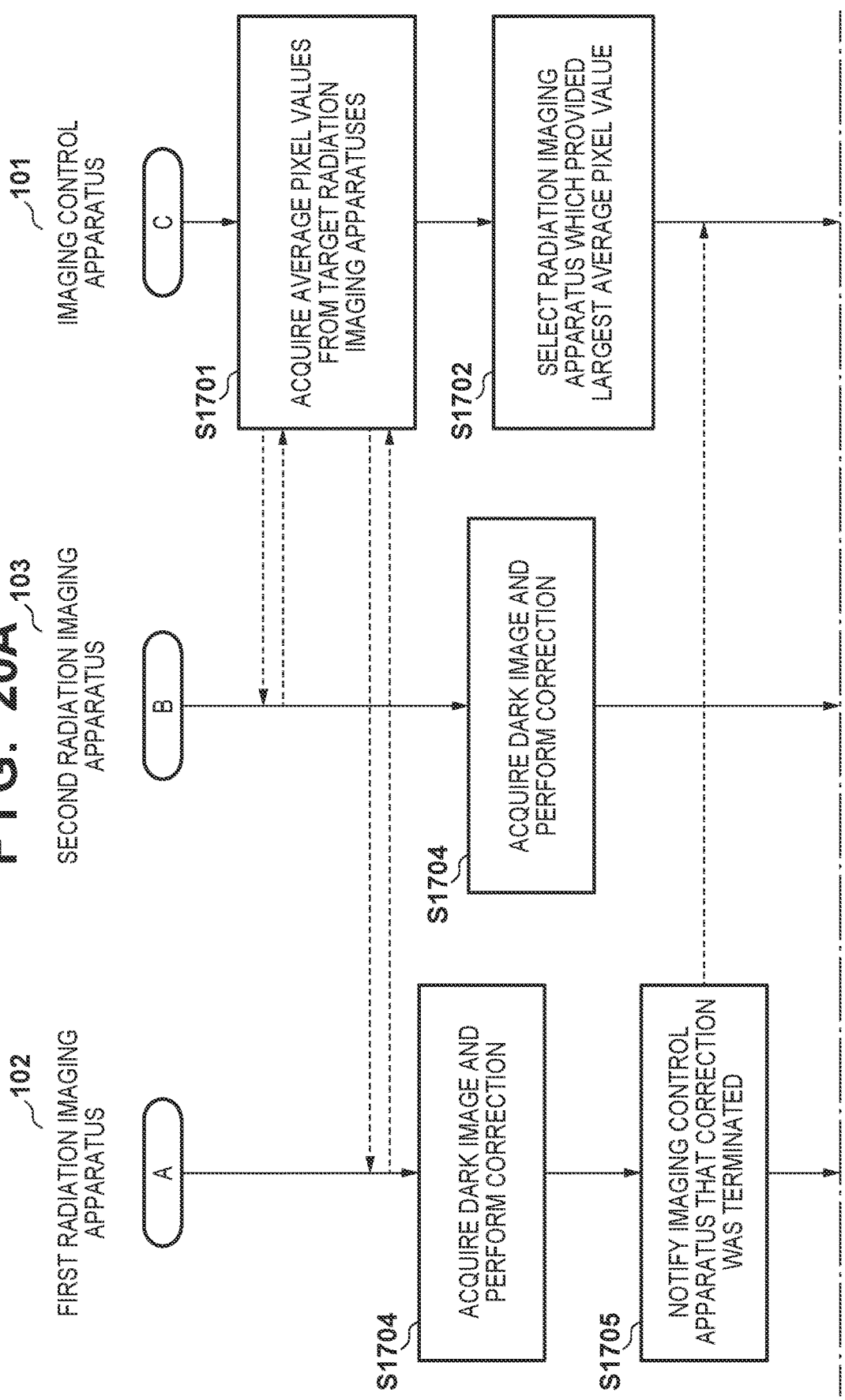

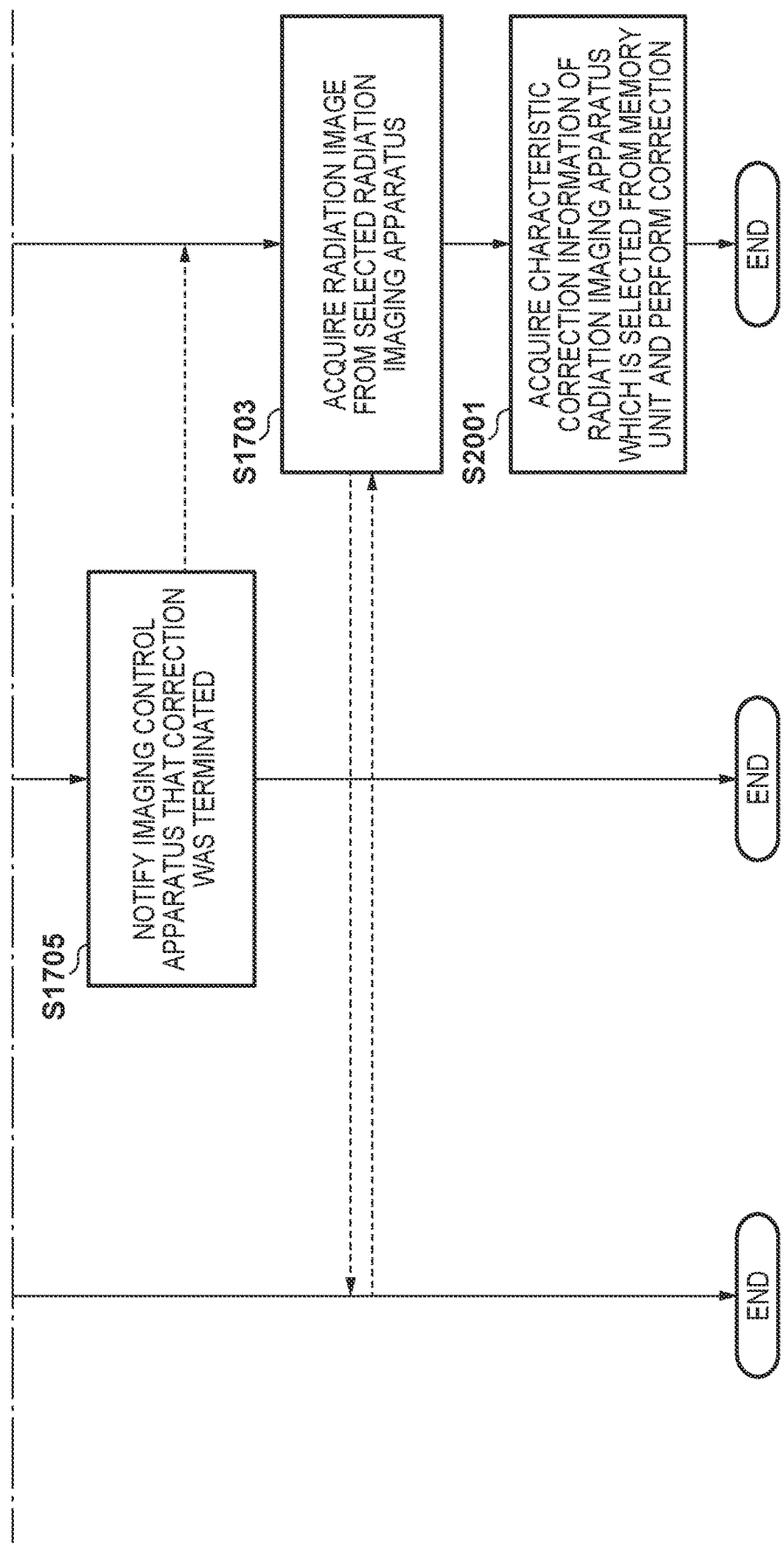

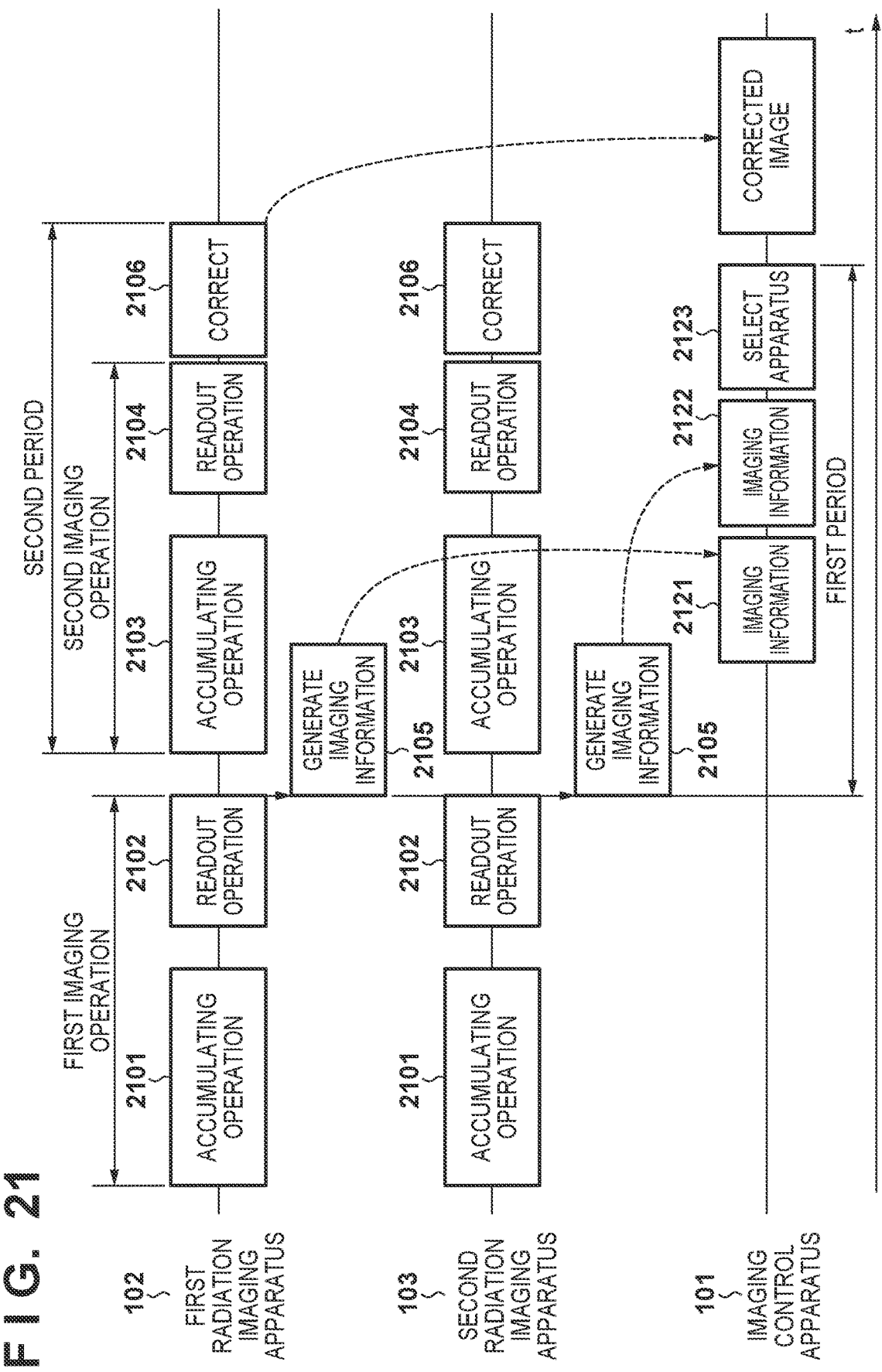

RADIATION IMAGING SYSTEM, IMAGING APPARATUS, CONTROL APPARATUS, AND METHODS OF CONTROLLING THE SAME

CROSS-REFERENCE TO RELATED APPLICATIONS

This application is a Continuation of International Patent Application No. PCT/JP2017/035502, filed Sep. 29, 2017, which claims the benefit of Japanese Patent Application No. 2016-203038, filed Oct. 14, 2016, Japanese Patent Application No. 2016-203041, filed Oct. 14, 2016, and Japanese Patent Application No. 2017-050291, filed Mar. 15, 2017, all of which are hereby incorporated by reference herein in their entirety.

BACKGROUND OF THE INVENTION

Field of the Invention

The present invention relates to a radiation imaging system, an imaging apparatus, a control apparatus, and methods of controlling the same.

Background Art

In recent years, with the proliferation of radiation imaging apparatuses that generate digital radiation images based on emitted radiation, radiation imaging systems are shifting toward digitalization. The digitalization of radiation imaging systems allows image checking immediately after radiation imaging. This has greatly improved workflow as compared with an imaging method using films or a CR (Computed Radiography) apparatus, and has made it possible to perform radiation imaging in a short cycle.

Such a radiation imaging system is provided with a radiation imaging apparatus and an imaging control apparatus that receives and uses radiation images from the radiation imaging apparatus. The radiation image acquired by the radiation imaging apparatus is transmitted as image data to an external imaging control apparatus. In a usage pattern in which the user selects one of a plurality of radiation imaging apparatuses and executes radiation imaging, it is necessary to notify in advance the imaging control apparatus of a specific radiation imaging apparatus from which image data should be acquired. Upon communication with the notified radiation imaging apparatus, the imaging control apparatus acquires image data. When the user uses a radiation imaging apparatus different from the notified radiation imaging apparatus, the imaging control apparatus cannot acquire any radiation image.

The radiation imaging system disclosed in PTL 1 enables a plurality of radiation imaging apparatuses to perform imaging, causes an imaging control apparatus to acquire radiation images from all the plurality of radiation imaging apparatuses, and selectively uses significant radiation images.

CITATION LIST

Patent Literature

PTL 1: Japanese Patent No. 5577114

In the radiation imaging system disclosed in PTL 1, however, the imaging control apparatus receives radiation images from all the radiation imaging apparatuses that have executed radiation imaging. For this reason, it takes time to display images obtained by radiation imaging or shift to next radiation imaging. This makes it impossible to perform radiation imaging in a short cycle.

SUMMARY OF INVENTION

An embodiment of the present invention discloses a radiation imaging system that includes a plurality of usable radiation imaging apparatuses and can perform radiation imaging in a short cycle.

A radiation imaging system according to one aspect of the present invention includes the following arrangement. That is, a radiation imaging system includes a plurality of imaging apparatuses configured to generate images based on radiation emitted from a radiation generator and a control apparatus configured to communicate with the plurality of imaging apparatuses, wherein each of the plurality of imaging apparatuses includes a generating unit configured to generate imaging information with a smaller data size than an image obtained by an imaging operation based on the image, and the control apparatus includes an information acquiring unit configured to acquire the imaging information from each of the plurality of imaging apparatuses, and a selecting unit configured to select, from the plurality of imaging apparatuses, an imaging apparatus for acquiring an image obtained by an imaging operation based on the imaging information acquired by the information acquiring unit.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 3A and 3B are flowcharts showing a radiation imaging operation according to the first embodiment;

FIG. 4 is a flowchart showing a radiation image acquiring operation according to the first embodiment;

FIGS. 6A and 6B are flowcharts showing a radiation image acquiring operation according to the second embodiment;

FIG. 7 is a flowchart showing a radiation image acquiring operation according to the third embodiment;

FIG. 8 is a flowchart showing a radiation image acquiring operation according to the fourth embodiment;

FIG. 9 is a flowchart showing a radiation image acquiring operation according to the fifth embodiment;

FIG. 10 is a flowchart showing a radiation image acquiring operation according to the sixth embodiment;

FIGS. 16A and 16B are flowcharts showing a radiation imaging operation according to the ninth embodiment;

FIG. 17 is a flowchart showing a radiation image acquiring operation according to the ninth embodiment;

FIG. 18 is a block diagram showing an example of the arrangement of a radiation imaging system according to the 10th embodiment;

FIGS. 19A and 19B are flowcharts showing an example of a radiation imaging operation according to the 10th embodiment;

FIGS. 20A and 20B are flowcharts showing an example of a radiation image acquiring/characteristic correcting operation according to the 10th embodiment; and FIG. 21 is a timing chart showing an example of timing of an imaging operation, generation of imaging information, and selection of a radiation imaging apparatus.

DESCRIPTION OF THE EMBODIMENTS

The preferred embodiments of the present invention will be described below with reference to the accompanying drawings. The following embodiments do not limit the present invention according to the appended claims, and not all combinations of characteristic features described in the embodiments are essential to the solving means of the present invention.

First Embodiment

Figure 1:
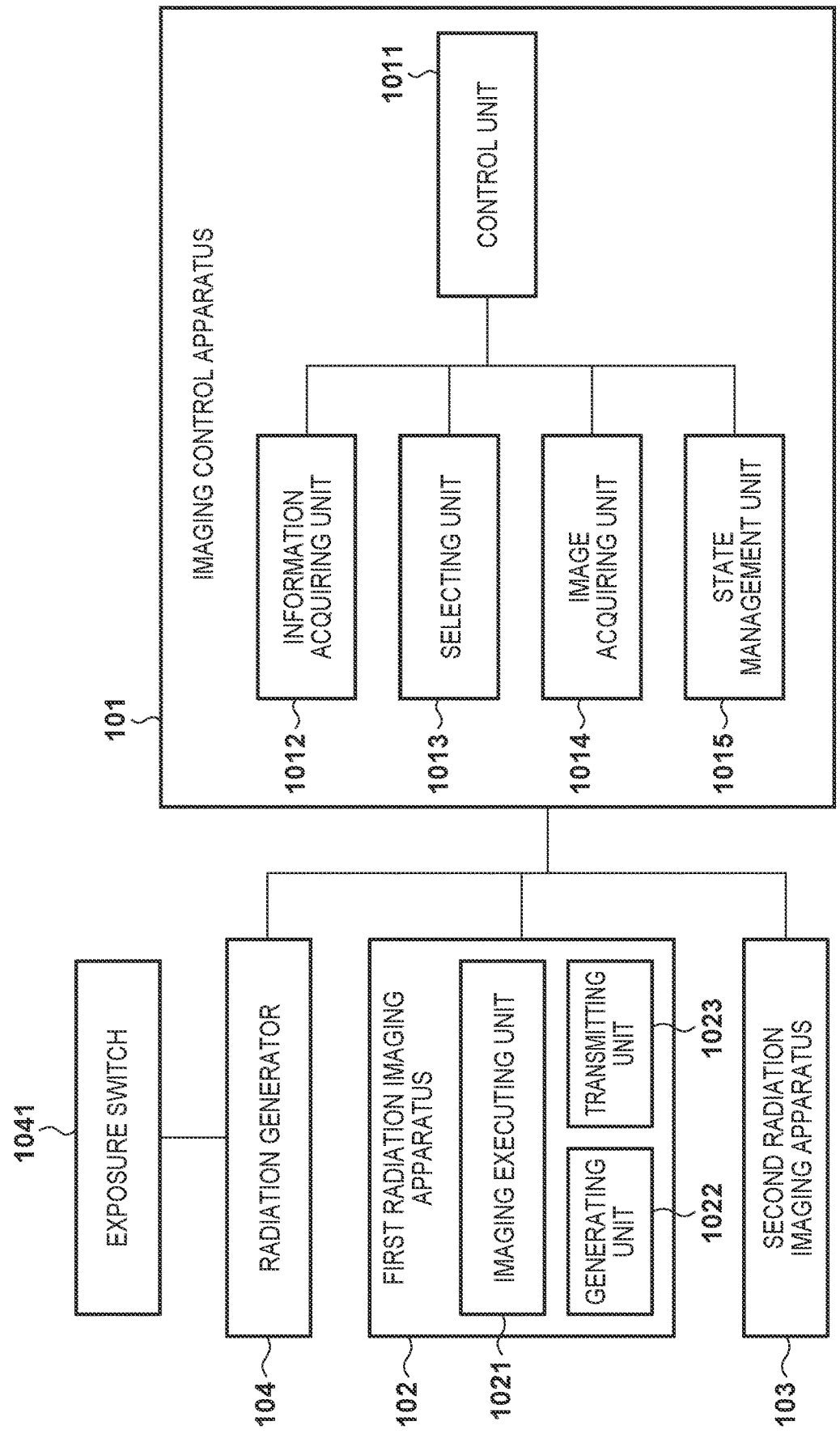
FIG. 1 is a block diagram showing an example of the functional arrangement of a radiation imaging system according to the first embodiment.

FIG. 1 is a block diagram showing an example of the functional arrangement of a radiation imaging system according to the first embodiment. The radiation imaging system according to this embodiment includes a radiation generator 104, a plurality of imaging apparatuses that generate images based on radiation emitted from the radiation generator 104, and a control apparatus that communicates with these imaging apparatuses. This embodiment exemplifies an imaging control apparatus 101 as the control apparatus, and also exemplifies a first radiation imaging apparatus 102 and a second radiation imaging apparatus 103 as the plurality of imaging apparatuses. The imaging control apparatus 101 controls radiation imaging by communicating with the connected first radiation imaging apparatus 102 and the second radiation imaging apparatus 103. The imaging control apparatus 101 also communicates with the radiation generator 104 to acquire information at the time of irradiation with radiation from the radiation generator 104. Note that the number of radiation imaging apparatuses is not limited to two but may be three or more. This embodiment will exemplify an arrangement including two radiation imaging apparatuses.

The first radiation imaging apparatus 102 and the second radiation imaging apparatus 103 shift to an imaging enabled state in response to an instruction from the imaging control apparatus 101, and execute radiation imaging in synchronism with the radiation generator 104. With this synchronization, the first radiation imaging apparatus 102 and the second radiation imaging apparatus 103 respectively generate radiation images based on radiation emitted from the radiation generator 104. In the first radiation imaging apparatus 102, an imaging executing unit 1021 executes an imaging operation in synchronism with the radiation generator 104 to obtain a radiation image. Based on the radiation image obtained by the imaging operation, a generating unit 1022 generates imaging information with a smaller data size than the radiation image. The imaging control apparatus 101 (selecting unit 1013) uses the imaging information to select a radiation imaging apparatus to acquire a radiation image. A transmitting unit 1023 transmits the imaging information generated by the generating unit 1022 to the imaging control apparatus 101 as an external apparatus. The transmitting unit 1023 also transmits the radiation image obtained by the imaging operation to an external apparatus (imaging control apparatus 101) in accordance with a request from the external apparatus. The second radiation imaging apparatus 103 has a similar functional arrangement.

In the imaging control apparatus 101, a control unit 1011 controls an information acquiring unit 1012, the selecting unit 1013, an image acquiring unit 1014, and a state management unit 1015. The information acquiring unit 1012 acquires imaging information from each of a plurality of radiation imaging apparatuses (the first radiation imaging apparatus 102 and the second radiation imaging apparatus 103), and acquires information at the time of irradiation with radiation from the radiation generator 104. The selecting unit 1013 selects one radiation imaging apparatus for acquiring a radiation image obtained by an imaging operation from the plurality of radiation imaging apparatuses (the first radiation imaging apparatus 102 and the second radiation imaging apparatus 103) based on the imaging information acquired by the information acquiring unit 1012. The image acquiring unit 1014 acquires a radiation image from one radiation imaging apparatus selected by the selecting unit 1013. The state management unit 1015 communicates with the first radiation imaging apparatus 102 or the second radiation imaging apparatus 103 to manage and control the state of each apparatus.

The radiation generator 104 transmits an irradiation start notification to all the usable radiation imaging apparatuses in accordance with the ON operation of an exposure switch 1041. Each radiation imaging apparatus that has received the irradiation start notification starts an imaging operation (electric charge accumulation), and transmits an irradiation permission notification to the radiation generator 104. The radiation generator 104 receives irradiation permission notifications from all the usable radiation imaging apparatuses (the first radiation imaging apparatus 102 and the second radiation imaging apparatus 103 in this embodiment) and executes irradiation with radiation. This operation establishes synchronization between the radiation generator 104 and the radiation imaging apparatuses 102 and 103.

Figure 2:
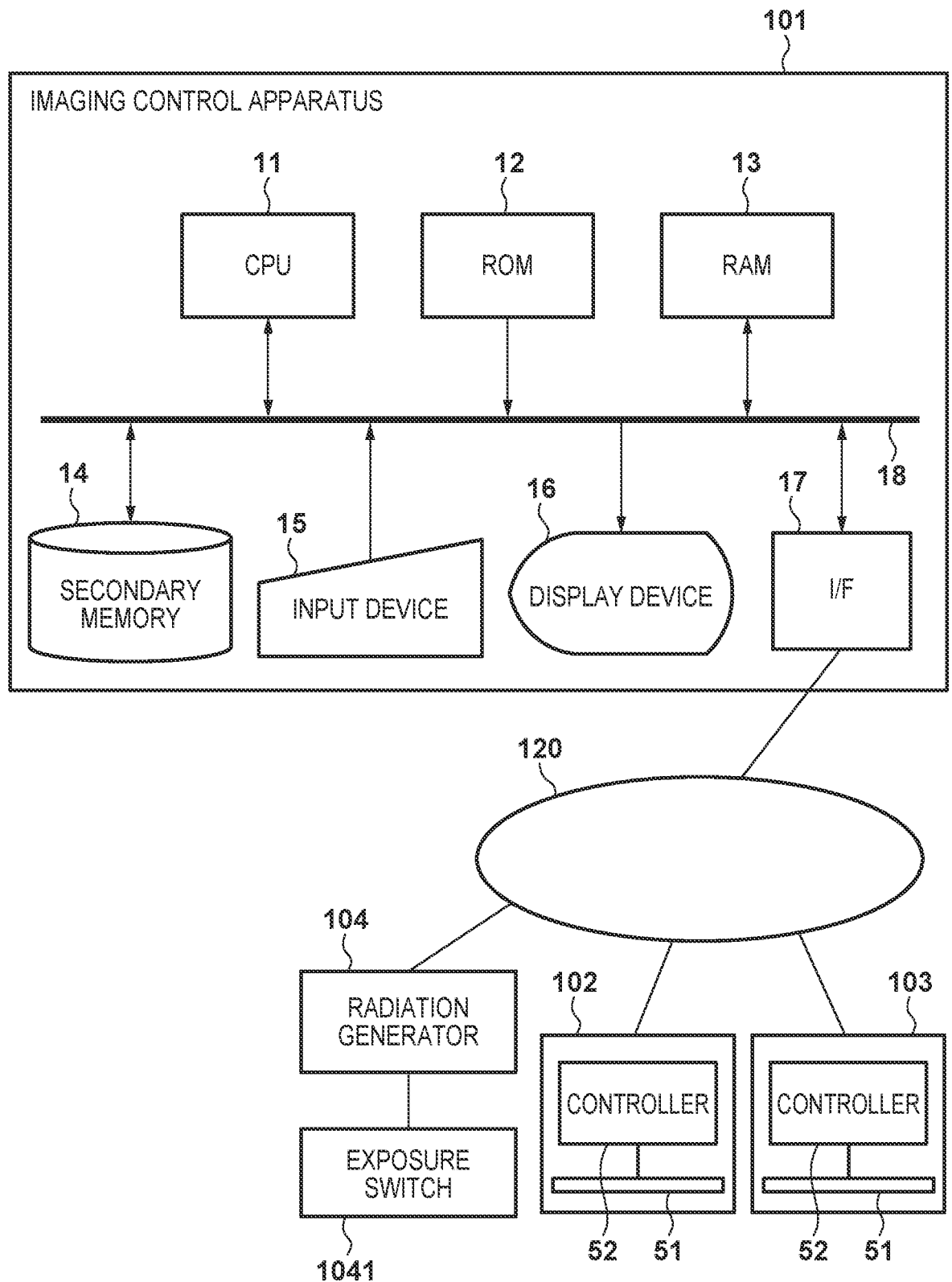
FIG. 2 is a block diagram showing an example of the hardware arrangement of the radiation imaging system according to the first embodiment.

FIG. 2 is a block diagram showing an example of the hardware arrangement of the radiation imaging system according to the first embodiment. In the imaging control apparatus 101, a CPU 11 implements each functional unit of the imaging control apparatus 101 shown in FIG. 1 by executing a corresponding program stored in a ROM 12 or a RAM 13. The ROM 12 is a read only memory, and the RAM 13 is a random access memory. A secondary memory 14 is formed from, for example, a hard disk, and stores, for example, the radiation images received from the radiation imaging apparatuses 102 and 103. A program stored in the secondary memory 14 is loaded into the RAM 13 and executed by the CPU 11 as needed. An input device 15 includes a pointing device and a keyboard, and accepts the operation of the user. A display device 16 is, for example, a liquid crystal display device, and displays radiation images and the like. An interface unit 17 connects the imaging control apparatus 101 to a network 120. The above components are communicably connected to each other via a bus 18.

The network 120 communicably connects the imaging control apparatus 101, the first radiation imaging apparatus 102, the second radiation imaging apparatus 103, and the radiation generator 104 to each other. The network 120 may take any form such as a wired network or wireless network. In addition, the network 120 or dedicated wired/wireless connection may be used for communication to establish synchronization between the radiation generator 104 and the radiation imaging apparatuses 102 and 103 described above.

The first radiation imaging apparatus 102 includes a radiation detection panel 51 and a controller 52. The radiation detection panel 51 is formed from, for example, an FPD (Flat Panel Detector), and generates a radiation image by generating an electrical signal corresponding to the dose of radiation. The controller 52 reads out a signal from the radiation detection panel 51 and generates a radiation image. In addition, the controller 52 generates imaging information with a smaller data size than a radiation image based on the radiation image and transmits the information to the imaging control apparatus 101. The controller 52 includes, for example, a CPU and a memory. The controller 52 controls imaging by the radiation detection panel 51, processes acquired images, and implements each functional unit shown in FIG. 1. The second radiation imaging apparatus 103 has a similar arrangement as that described above.

FIGS. 3A and 3B are flowcharts showing an example of an operation from preparation for radiation imaging to the execution of radiation imaging, performed by the imaging control apparatus 101, the first radiation imaging apparatus 102, and the second radiation imaging apparatus 103. Note that the CPU 11 implements the operation of the imaging control apparatus 101 by executing a predetermined program. The CPU (not shown) in the controller 52 implements the operation of the first radiation imaging apparatus 102 and the second radiation imaging apparatus 103 by executing predetermined programs stored in a memory (not shown).

In step S101, the first radiation imaging apparatus 102 and the second radiation imaging apparatus 103 are set in the standby state. In the standby state, communication (for example, communication via the network 120) is established between the radiation imaging apparatuses and the imaging control apparatus 101. In step S102, the imaging control apparatus 101 (the state management unit 1015) transmits a transition instruction for transition to the imaging enabled state to all usable radiation imaging apparatuses. In this embodiment, the first radiation imaging apparatus 102 and the second radiation imaging apparatus 103 are usable radiation imaging apparatuses.

In step S103, the first radiation imaging apparatus 102 and the second radiation imaging apparatus 103 transition to the imaging enabled state in accordance with the transition instruction from the imaging control apparatus 101, and notify the imaging control apparatus 101 of the transition to the imaging enabled state. In step S104, the imaging executing units 1021 of the first radiation imaging apparatus 102 and the second radiation imaging apparatus 103 establish synchronization with the radiation generator 104, and execute radiation imaging. In step S105, the first radiation imaging apparatus 102 and the second radiation imaging apparatus 103 each notify the imaging control apparatus 101 of the execution of the radiation imaging.

FIG. 4 is a flowchart showing an example of an operation from the execution of radiation imaging by the first radiation imaging apparatus 102 and the second radiation imaging apparatus 103 to the acquisition of radiation images by the imaging control apparatus 101.

In step S201, the generating units 1022 of the first radiation imaging apparatus 102 and the second radiation imaging apparatus 103 calculate the statistic information of the pixel values of the generated radiation images as imaging information. The transmitting units 1023 transmit the calculated statistic information as imaging information to the imaging control apparatus 101. Assume that the average value (to be referred to as the average pixel value) of pixel values is used as an example of statistic information. Obviously, statistic information is not limited to them. For example, the maximum value, median value, or variance value of pixel values may be used. Alternatively, it is possible to use statistic information such as the maximum value of the differences between the pixel values of adjacent pixels or the width between the maximum value and the minimum values of pixel values. In addition, two or more pieces of statistic information may be calculated. Note that pixel values may be luminance values or density values. In step S202, the imaging control apparatus 101 (the information acquiring unit 1012) acquires the average pixel values calculated in step S201 from the first radiation imaging apparatus 102 and the second radiation imaging apparatus 103.

In step S203, the imaging control apparatus 101 (the selecting unit 1013) compares the average pixel values acquired in step S202 to select a radiation imaging apparatus that has provided the largest average pixel value. Although the above description has exemplified the arrangement configured to select a radiation imaging apparatus that has provided the largest average pixel value, this is not exhaustive. For example, the arrangement may be configured to select a radiation imaging apparatus that has provided statistic information nearest to a preset threshold. In addition, a radiation imaging apparatus may be selected by comparing a plurality of pieces of statistic information. Comparison between a plurality of pieces of statistic information may use, for example, combinations of "average pixel values" and "widths between maximum values and minimum values of pixel values". In this case, determination is basically performed by using "average pixel values". If there is not much difference between average values, determination is performed by using "widths between maximum values and minimum values of pixel values". When, for example, narrowed irradiation regions are irradiated with radiation, much difference does not easily appear between average pixel values of radiation images. In such a case, in additional consideration of "widths between maximum values and minimum values of pixel values", a radiation imaging apparatus that provides a significant radiation image is selected. Obviously, this is not exhaustive. For example, a radiation imaging apparatus may be normally selected by referring to "widths between maximum values and minimum values of pixel values", and when no significant difference appears, a radiation imaging apparatus may be selected in additional consideration of "average pixel values". This method is effective when no significant difference appears between "widths between maximum values and minimum values of pixel values" between radiation images due to some kind of noise or the like. Obviously, it is possible to use a combination of other types of statistic information. In addition, when a comparison result indicates no difference and hence does not allow selection of one radiation imaging apparatus, any radiation imaging apparatus that has notified first the execution of radiation imaging may be selected.

In step S204, the imaging control apparatus 101 (the image acquiring unit 1014) acquires a radiation image from the radiation imaging apparatus (the first radiation imaging apparatus 102 in this case) selected in step S203. That is, the imaging control apparatus 101 requests the first radiation imaging apparatus 102 to transmit an image, and the transmitting unit 1023 of the first radiation imaging apparatus 102 transmits the radiation image to the imaging control apparatus 101 in accordance with the request for the image from the imaging control apparatus 101.

As described above, in the system that executes radiation imaging by setting a plurality of radiation imaging apparatuses in the imaging enabled state, the imaging control apparatus 101 selects a radiation imaging apparatus from which a radiation image should be acquired based on imaging information (for example, average pixel values) with a smaller data size than the radiation image. The imaging control apparatus 101 acquires a radiation image from the selected radiation imaging apparatus, and hence can shorten a radiation imaging cycle as compared with the arrangement configured to acquire radiation images from all radiation imaging apparatuses. This can implement a radiation imaging system that can perform radiation imaging in a short cycle while reducing the chance of unnecessary exposure to radiation due to re-imaging.

Second Embodiment

According to the first embodiment, the selecting unit 1013 selects a radiation imaging apparatus that has performed imaging under irradiation with radiation based on the imaging information (statistic information) acquired by the selecting unit 1013, and the image acquiring unit 1014 acquires a radiation image from the selected radiation imaging apparatus. The second embodiment will exemplify an arrangement configured to acquire a radiation image from a radiation imaging apparatus automatically selected in this manner and then acquire a radiation image from another radiation imaging apparatus in accordance with, for example, an instruction from the user.

Figure 5:
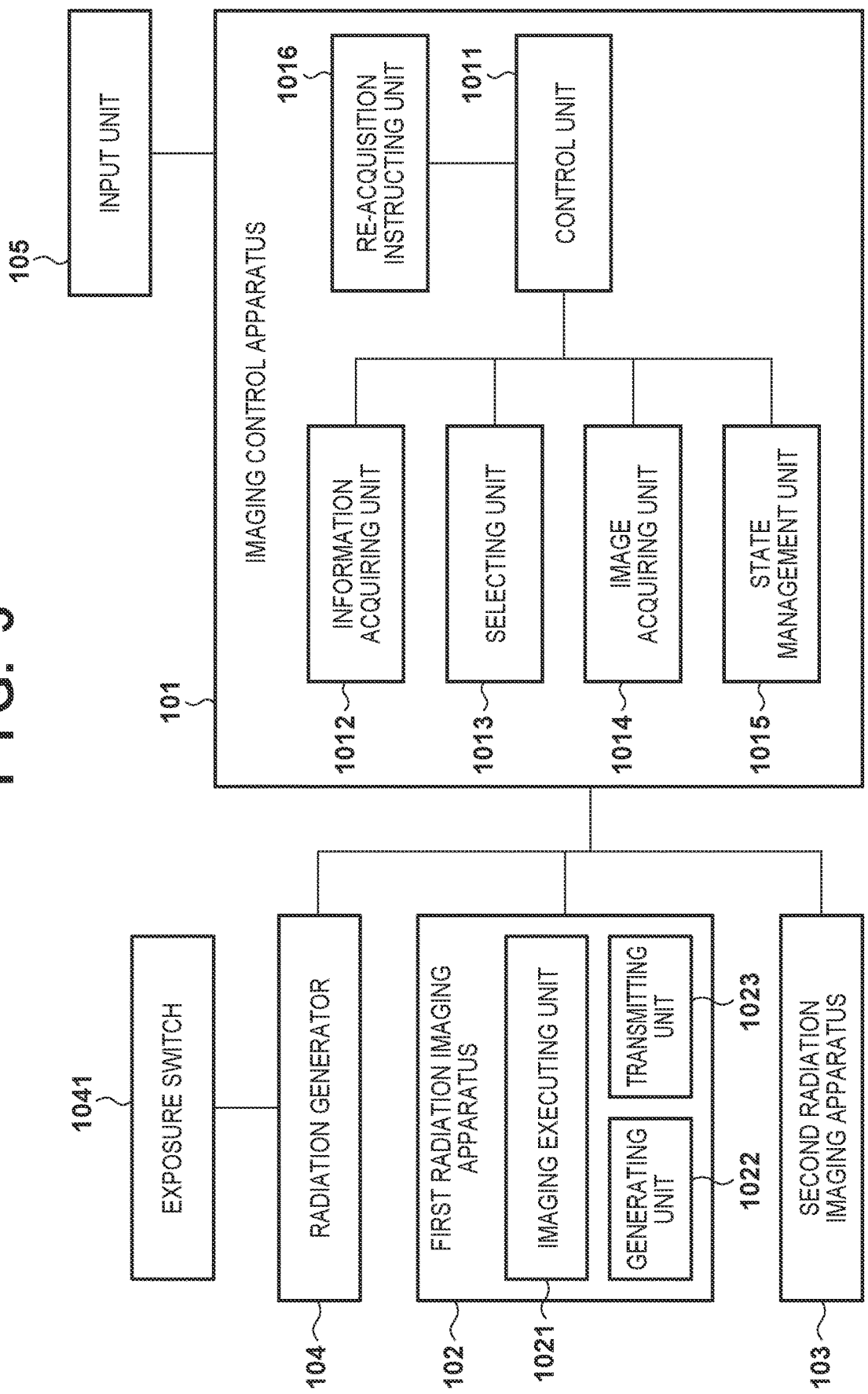
FIG. 5 is a block diagram showing an example of the functional arrangement of a radiation imaging system according to the second embodiment.

FIG. 5 is a block diagram showing an example of the functional arrangement of a radiation imaging system according to the second embodiment. The same reference numerals denote similar components as those in the first embodiment (FIG. 1). Note that the hardware arrangement of the radiation imaging system according to the second embodiment is similar to that of the first embodiment (FIG. 2). Referring to FIG. 5, the second embodiment includes an input unit 105 and a re-acquisition instructing unit 1016 in addition to the arrangement of the first embodiment. The input unit 105 accepts external operation inputs via a user interface or an input device 15 (a mouse and a keyboard) provided for a display device 16. After an image acquiring unit 1014 acquires a radiation image from one radiation imaging apparatus selected by a selecting unit 1013, the re-acquisition instructing unit 1016 instructs a control unit 1011 to acquire a radiation image from another radiation imaging apparatus in accordance with a predetermined operation input from the input unit 105. In accordance with the instruction from the re-acquisition instructing unit 1016, the control unit 1011 instructs the image acquiring unit 1014 to acquire a radiation image from a radiation imaging apparatus from which no radiation image has been acquired. The image acquiring unit 1014 acquires a radiation image from the radiation imaging apparatus in accordance with the instruction from the control unit 1011. Obviously, the re-acquisition instructing unit 1016 may directly instruct the image acquiring unit 1014 to designate a radiation image and acquire the radiation image.

An operation from preparation for radiation imaging to the execution of radiation imaging performed by an imaging control apparatus 101, a first radiation imaging apparatus 102, and a second radiation imaging apparatus 103 is similar to that in the first embodiment (FIGS. 3A and 3B). FIGS. 6A and 6B are flowcharts showing an example of an operation according to the second embodiment, that is, the acquisition of a radiation image by the imaging control apparatus 101 upon execution of radiation imaging by the first radiation imaging apparatus 102 and the second radiation imaging apparatus 103. Note that the same step numbers denote similar operations as in the first embodiment (FIG. 4).

In step S204, the image acquiring unit 1014 acquires a radiation image from a radiation imaging apparatus (the first radiation imaging apparatus 102 in this case) selected by the selecting unit 1013 based on imaging information (statistic information). Subsequently, in step S301, the control unit 1011 determines whether a re-acquisition instruction is received from the re-acquisition instructing unit 1016. If a re-acquisition instruction is received, the process advances to step S302. If no re-acquisition instruction is received, the process advances to step S304. Although in this case, a re-acquisition instruction is input in accordance with a user operation with the input unit 105, this is not exhaustive. For example, if no object image can be recognized upon analysis of the radiation image acquired by the image acquiring unit 1014, the control unit 1011 may automatically generate a re-acquisition instruction.

In step S302, the selecting unit 1013 selects one radiation imaging apparatus other than a radiation imaging apparatus from which a radiation image has been acquired. In this case, the second radiation imaging apparatus 103 is selected as a radiation imaging apparatus other than the first radiation imaging apparatus 102 from which a radiation image has been acquired. If there are three or more radiation imaging apparatuses, the user may select a radiation imaging apparatus with the input unit 105. In this case, a list of radiation imaging apparatuses that can be selected (radiation imaging apparatuses from which no radiation image has been acquired) may be displayed to allow the user to select a radiation imaging apparatus from the list. Alternatively, the selecting unit 1013 may select a radiation imaging apparatus from radiation imaging apparatuses from which radiation images have been acquired based on the imaging information acquired by an information acquiring unit 1012. For example, the selecting unit 1013 may select a radiation imaging apparatus that has provided the largest average pixel value from radiation imaging apparatuses from which no radiation image has been acquired.

In step S303, the image acquiring unit 1014 acquires a radiation image from the radiation imaging apparatus (the second radiation imaging apparatus 103 in this case) selected by the selecting unit 1013 in step S302. That is, when the image acquiring unit 1014 requests the second radiation imaging apparatus 103 to transmit a radiation image, the transmitting unit 1023 of the second radiation imaging apparatus 103 transmits the radiation image acquired by the imaging executing unit 1021 to the imaging control apparatus 101 in accordance with this request. In step S304, the control unit 1011 determines whether the radiation imaging should be terminated. For example, the user can issue an instruction to terminate radiation imaging with the input device 15. If radiation imaging should not be terminated, the process returns to step S301 to repeat the processing from step S301. In contrast, if radiation imaging should be terminated, the processing in this flowchart is terminated.

As described above, according to the second embodiment, after a radiation image is acquired from one radiation imaging apparatus selected based on imaging information, a radiation image can be acquired from another radiation imaging apparatus. Even if, therefore, an error occurs in automatic selection of radiation imaging, a radiation image can be acquired without performing re-imaging.

Third Embodiment

In the first embodiment, statistic information obtained from a radiation image is used as imaging information for determining a specific radiation imaging apparatus from which a radiation image should be acquired. The third embodiment will exemplify an arrangement configured to obtain statistic information from an image (pixel group) that is generated by a generating unit 1022 based on a radiation image and having a smaller data size than a radiation image. Note that the functional arrangement and the hardware arrangement of a radiation imaging system according to the third embodiment are similar to those of the first embodiment (FIGS. 1 and 2).

The operation from preparation for radiation imaging to the execution of radiation imaging performed by an imaging control apparatus 101, a first radiation imaging apparatus 102, and a second radiation imaging apparatus 103 is similar to that in the first embodiment (FIGS. 3A and 3B). FIG. 7 is a flowchart showing an example of an operation according to the third embodiment, that is, the acquisition of a radiation image by the imaging control apparatus 101 after execution of radiation imaging by the first radiation imaging apparatus 102 and the second radiation imaging apparatus 103.

In step S401, the generating unit 1022 of each of the first radiation imaging apparatus 102 and the second radiation imaging apparatus 103 calculates, as imaging information, statistic information of pixel values from an image obtained by thinning out the radiation image acquired by an imaging executing unit 1021. Assume that in this case, the average value of pixel values is calculated as statistic information. In addition, although a thinned-out image is used as an image from which statistic information is to be calculated (an image with a smaller data size than a radiation image), this is not exhaustive. For example, the generating unit 1022 may calculate statistic information from a reduced image of a radiation image, pixels at one or more predetermined coordinates, pixels in a region of interest, or the like. A reduced image is generated by, for example, calculating the pixel value of one pixel from the pixel values of a plurality of pixels (for example, calculating the average value of neighboring pixels). A region of interest is detected by analyzing a radiation image using a known method. Although the average value of pixel values is used as an example of statistic information, this is not exhaustive. As in the first embodiment, for example, statistic information such as the maximum value, median value, or variance value of pixel values may be used. Alternatively, it is possible to use statistic information such as the maximum value of the differences between the pixel values of adjacent pixels or the width between the maximum value and the minimum values of pixel values. In addition, two or more pieces of statistic information may be calculated. Note that pixel values may be luminance values or density values.

In step S402, the imaging control apparatus 101 (an information acquiring unit 1012) acquires the average pixel values calculated in step S401 from the first radiation imaging apparatus 102 and the second radiation imaging apparatus 103 (transmitting units 1023). In step S403, a selecting unit 1013 compares the average pixel values acquired in step S402 and selects a radiation imaging apparatus with the largest average pixel value. Although in this case, a radiation imaging apparatus with the largest average pixel value is selected, this is not exhaustive. As in the first embodiment, a radiation imaging apparatus from which statistic information nearest to a preset threshold is acquired may be selected. Alternatively, a plurality of pieces of statistic information may be compared for selection. When a comparison result indicates no difference and hence does not allow selection of one radiation imaging apparatus, any radiation imaging apparatus that has notified first the execution of radiation imaging may be selected. In step S404, the imaging control apparatus 101 (an image acquiring unit 1014) acquires a radiation image from the radiation imaging apparatus (the first radiation imaging apparatus 102 in this case) selected by the selecting unit 1013 in step S403.

As described above, according to the third embodiment, imaging information (for example, statistic information of pixel values) to be compared to select a radiation imaging apparatus from which a radiation image should be acquired is generated from partial information of the radiation image. This reduces the processing load for the calculation of imaging information by a radiation imaging apparatus.

Fourth Embodiment

In the first to third embodiments, the information acquiring unit 1012 acquires statistic information concerning a radiation image from a radiation imaging apparatus. In the fourth embodiment, an information acquiring unit 1012 acquires from a plurality of radiation imaging apparatuses, as imaging information, an image generated based on a radiation image and having a smaller data size than the radiation image, and calculates statistic information from the acquired imaging information (image). Note that the functional arrangement and hardware arrangement of the radiation imaging system according to the fourth embodiment are similar to those of the first embodiment (FIGS. 1 and 2). Although the data size of imaging information in this arrangement may become larger than that in the arrangements according to the first to third embodiments, each of which uses statistic information such as an average pixel value as imaging information acquired from all radiation imaging apparatuses, it is possible to reduce the processing load on each radiation imaging apparatus.

The operation from preparation for radiation imaging to the execution of radiation imaging performed by an imaging control apparatus 101, a first radiation imaging apparatus 102, and a second radiation imaging apparatus 103 is similar to that in the first embodiment (FIGS. 3A and 3B). FIG. 8 is a flowchart showing an example of an operation according to the fourth embodiment, that is, the acquisition of a radiation image by the imaging control apparatus 101 after execution of radiation imaging by the first radiation imaging apparatus 102 and the second radiation imaging apparatus 103.

In step S501, a generating unit 1022 of each of the first radiation imaging apparatus 102 and the second radiation imaging apparatus 103 generates, as imaging information, an image based on a radiation image and having a smaller data size than the radiation image. For example, an image obtained by thinning out the radiation image generated by an imaging executing unit 1021 is extracted and used as imaging information. Although in this case, the thinned-out image is exemplified as an image with a small data size, this is not exhaustive. For example, part of a radiation image may be a reduced image of a radiation image, pixels at preset coordinates, or an image in a region of interest in a radiation image. In step S502, the imaging control apparatus 101 (the information acquiring unit 1012) acquires the thinned-out image extracted in step S501 from each of the first radiation imaging apparatus 102 and the second radiation imaging apparatus 103.

In step S503, a selecting unit 1013 generates predetermined statistic information from the pixel values of each image with a small data size, and selects one radiation imaging apparatus based on the generated statistic information. For example, the selecting unit 1013 calculates statistic information (the average value in this case) of pixel values from each thinned-out image acquired in step S502, and selects one radiation imaging apparatus based on the statistic information. Although in this case, an average value is used as the statistic information of pixel values, this is not exhaustive. For example, statistic information such as the maximum value, median value, or variance value of pixel values may be used. Alternatively, it is possible to use statistic information such as the maximum value of the differences between the pixel values of adjacent pixels or the width between the maximum value and the minimum values of pixel values. In addition, two or more pieces of statistic information may be calculated. Note that pixel values may be luminance values or density values.

In step S504, the selecting unit 1013 compares the average pixel values acquired in step S503, and selects a radiation imaging apparatus that has generated a thinned-out image with the largest average pixel value. Although in this case, for example, a radiation imaging apparatus corresponding to the largest average pixel value is selected, this is not exhaustive. For example, as in the first embodiment, a radiation imaging apparatus that has provided a thinned-out image from which statistic information nearest to a preset threshold has been acquired may be selected. Alternatively, a plurality of pieces of statistic information may be compared for selection. When the comparison result obtained by the selecting unit 1013 indicates no difference and hence does not allow selection of one radiation imaging apparatus, any radiation imaging apparatus that has notified first the execution of radiation imaging may be selected. In step S505, the imaging control apparatus 101 (an image acquiring unit 1014) acquires a radiation image from the radiation imaging apparatus (the first radiation imaging apparatus 102 in this case) selected by the selecting unit 1013 in step S504.

As described above, the fourth embodiment can provide a similar effect to that of the first embodiment even by using part of a radiation image as information to be used for comparative selection of a radiation imaging apparatus from which a radiation image should be acquired.

Fifth Embodiment

The third embodiment uses a thinned-out image as partial information of a radiation image. The fifth embodiment uses an image portion, of a generated radiation image, which corresponds to an irradiation field as an example of partial information of the radiation image. That is, in the fifth embodiment, a radiation imaging apparatus is selected based on the statistic information of pixels corresponding to the irradiation field. Note that the functional arrangement and hardware arrangement of a radiation imaging system according to the fifth embodiment are similar to those of the first embodiment (FIGS. 1 and 2).

An operation from preparation for radiation imaging to the execution of radiation imaging performed by an imaging control apparatus 101, a first radiation imaging apparatus 102, and a second radiation imaging apparatus 103 is similar to that in the first embodiment (FIGS. 3A and 3B). FIG. 9 is a flowchart showing an example of an operation according to the fifth embodiment, that is, the acquisition of a radiation image by the imaging control apparatus 101 after execution of radiation imaging by the first radiation imaging apparatus 102 and the second radiation imaging apparatus 103.

In step S601, a generating unit 1022 of each of the first radiation imaging apparatus 102 and the second radiation imaging apparatus 103 detects an irradiation field as a range of irradiation with radiation by analyzing the acquired radiation image. In step S602, each of the first radiation imaging apparatus 102 and the second radiation imaging apparatus 103 calculates the average value of pixel values from the range of the irradiation field of the generated radiation image by using the irradiation field detected by analysis in step S601. Although the average value of pixel values is used as an example of statistic information, this is not exhaustive. As in the first embodiment, for example, statistic information such as the maximum value, median value, or variance value of pixel values may be used. Alternatively, it is possible to use statistic information such as the maximum value of the differences between the pixel values of adjacent pixels or the width between the maximum value and the minimum values of pixel values. In addition, two or more pieces of statistic information may be calculated. Note that pixel values may be luminance values or density values.

In step S603, the imaging control apparatus 101 (an information acquiring unit 1012) acquires the average pixel values calculated in step S602 from the first radiation imaging apparatus 102 and the second radiation imaging apparatus 103. Processing in steps S604 and S605 (selection of a radiation imaging apparatus by using the acquired imaging information (average pixel value) and acquisition of a radiation image from the selected radiation imaging apparatus) is similar to that in the first embodiment (steps S203 and S204 in FIG. 4).

As described above, imaging information obtained from the range of an irradiation field can be used as information used for comparative selection of a radiation imaging apparatus from which a radiation image should be acquired. Each radiation imaging apparatus is only required to calculate statistic information of the range of an irradiation field, and hence the load is reduced.

Sixth Embodiment

The fifth embodiment is configured to detect an irradiation field from the radiation image generated by each radiation imaging apparatus. However, this is not exhaustive. The sixth embodiment will exemplify an arrangement configured to determine an irradiation field in a radiation image based on information concerning irradiation with radiation from a radiation generator 104. The functional arrangement and hardware arrangement of a radiation imaging system according to the sixth embodiment are similar to those of the first embodiment (FIGS. 1 and 2). An operation from preparation for radiation imaging to the execution of radiation imaging performed by an imaging control apparatus 101, a first radiation imaging apparatus 102, and a second radiation imaging apparatus 103 is similar to that in the first embodiment (FIGS. 3A and 3B). FIG. 10 is a flowchart showing an example of an operation according to the sixth embodiment, from preparation for radiation imaging to the execution of radiation imaging, performed by the imaging control apparatus 101, the first radiation imaging apparatus 102, and the second radiation imaging apparatus 103.

In step S701, the imaging control apparatus 101 (a state management unit 1015) acquires information at the time of irradiation with radiation from the radiation generator 104, and notifies the first radiation imaging apparatus 102 and the second radiation imaging apparatus 103 of collimator information of the acquired information. Although in this case, collimator information is acquired and notified as an example of information concerning irradiation with radiation, this is not exhaustive. For example, such information may be irradiation field information calculated from the distance between the tube of the radiation generator 104 and the radiation imaging apparatus or the angle of the tube.

In step S702, each of the first radiation imaging apparatus 102 and the second radiation imaging apparatus 103 calculates an irradiation field from the collimator information notified in step S701, and calculates an average pixel value from the range of an irradiation field in the generated radiation image. Although in this case, an average pixel value is used as an example of statistic information, this is not exhaustive. As in the first embodiment, for example, statistic information such as the maximum value, median value, or variance value of pixel values may be used. Alternatively, it is possible to use statistic information such as the maximum value of the differences between the pixel values of adjacent pixels or the width between the maximum value and the minimum values of pixel values. In addition, two or more pieces of statistic information may be calculated. Note that pixel values may be luminance values or density values.

Processing in steps S703 to S705 (selection of a radiation imaging apparatus by using the acquired imaging information (average pixel value) and acquisition of a radiation image from the selected radiation imaging apparatus) are similar to that in the first embodiment (steps S202 and S204 in FIG. 4).

As described above, according to the sixth embodiment, an irradiation field as a range in which statistic information is calculated can be determined based on information concerning irradiation with radiation acquired from an external apparatus. This reduces the processing load as compared with the fifth embodiment configured to detect an irradiation field from a radiation image.

Seventh Embodiment

The first to sixth embodiments each are configured to acquire imaging information (statistic information, reduced images, partial images, and the like) with a smaller data size than a radiation image from each of the plurality of radiation imaging apparatuses and select a radiation imaging apparatus from which a radiation image should be acquired by comparing the imaging information. The plurality of radiation imaging apparatuses have individual differences in, for example, reception sensitivity of radiation and defective pixels. For this reason, even with irradiation with the same dose of radiation, the respective radiation imaging apparatuses may notify different pieces of imaging information. The seventh embodiment will exemplify an arrangement configured to more accurately select a radiation imaging apparatus in consideration of such individual differences between radiation imaging apparatuses.

Figure 11:
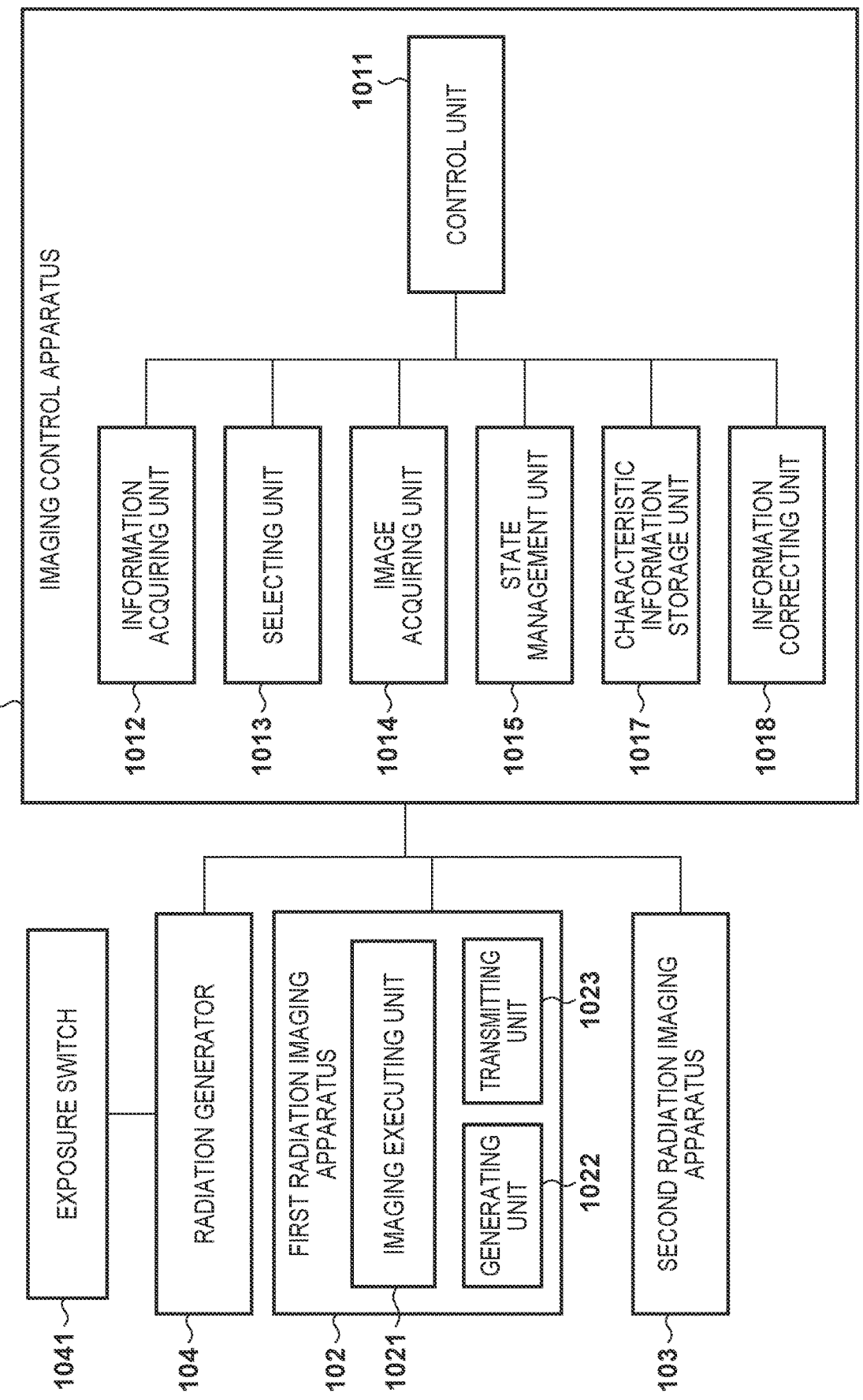
FIG. 11 is a block diagram showing an example of the functional arrangement of a radiation imaging system according to the seventh embodiment.

FIG. 11 is a block diagram showing an example of the functional arrangement of a radiation imaging system according to the seventh embodiment. The same reference numerals denote similar components to those in the first embodiment (FIG. 1). An imaging control apparatus 101 according to the seventh embodiment includes a characteristic information storage unit 1017 and an information correcting unit 1018 in addition to the arrangement of the first embodiment. Note that the hardware arrangement of the radiation imaging system according to the seventh embodiment is similar to that of the first embodiment (FIG. 2).

An information acquiring unit 1012 acquires characteristic information of each of a plurality of radiation imaging apparatuses as well as having a similar function to that of the first embodiment (acquisition of imaging information and information at the time of irradiation with radiation). The characteristic information storage unit 1017 stores characteristic information representing the characteristics of each of a plurality of radiation imaging apparatuses which are acquired by the information acquiring unit 1012. An example of characteristic information is, for example, sensitivity information representing a pixel value that can be converted when an element that receives radiation in a radiation imaging apparatus receives 1 mR (milliroentgen) of radiation. In addition, it is possible to use, as sensitivity information, for example, the ratio between a target value of an average pixel value that can be acquired when an imaging apparatus is irradiated with radiation under predetermined conditions and an average pixel value that was able to be actually acquired. In this case, the target value may be determined in accordance with the type of phosphor. Alternatively, an image (gain image) generated when radiation imaging is performed under predetermined conditions may be used as sensitivity information. Sensitivity information may be periodically updated or determined in a manufacturing process.

The information correcting unit 1018 corrects the imaging information acquired by the information acquiring unit 1012 from a plurality of radiation imaging apparatuses based on characteristic information stored in the characteristic information storage unit 1017. A selecting unit 1013 selects one radiation imaging apparatus from a plurality of radiation imaging apparatuses (a first radiation imaging apparatus 102 and a second radiation imaging apparatus 103 in this embodiment) based on the imaging information corrected by the information correcting unit 1018.

Figure 12:
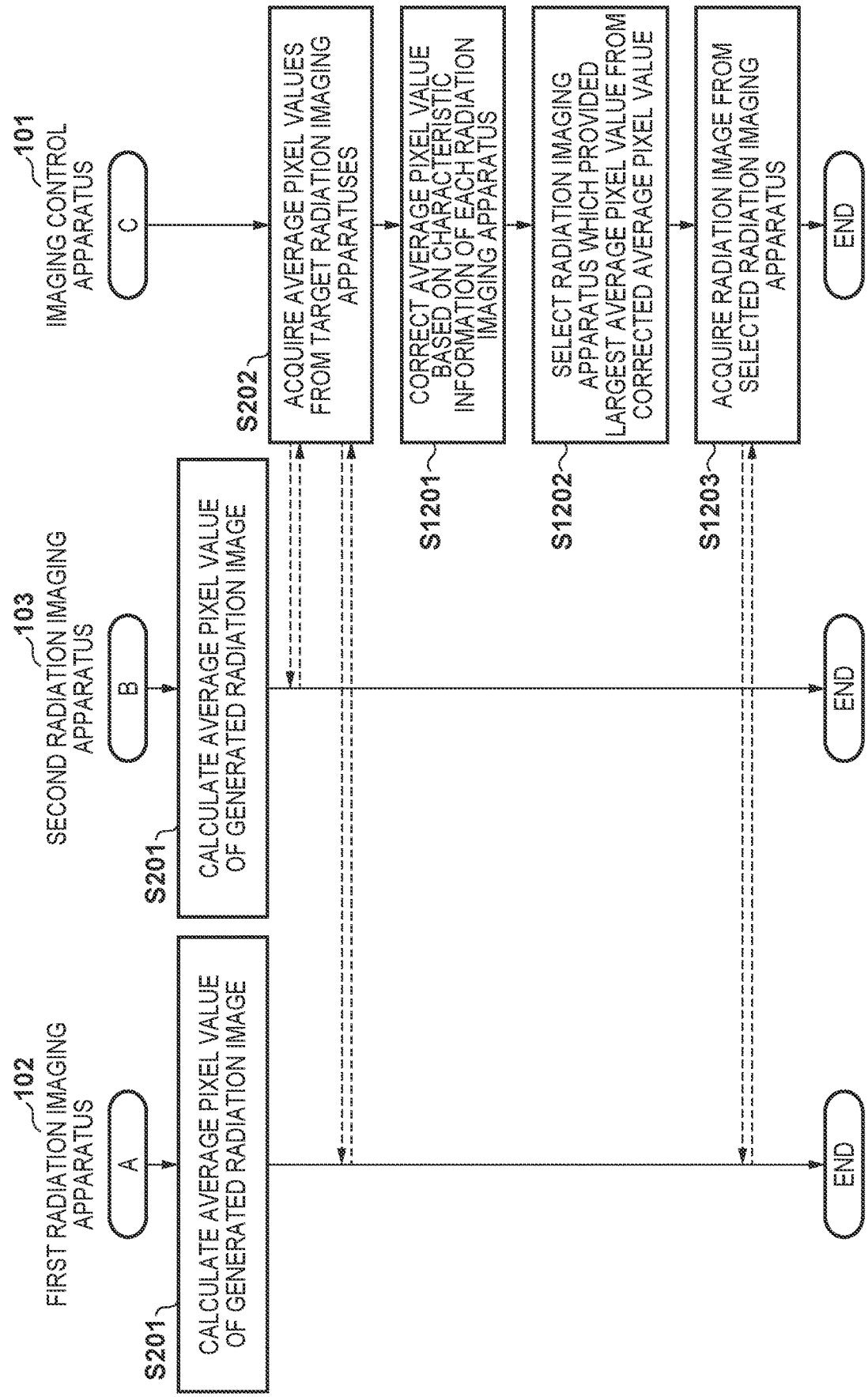
FIG. 12 is a flowchart showing a radiation image acquiring operation according to the seventh embodiment.

FIG. 12 is a flowchart showing an example of an operation from the execution of radiation imaging by the first radiation imaging apparatus 102 and the second radiation imaging apparatus 103 to the acquisition of a radiation image by the imaging control apparatus 101. Note that the operation from preparation for radiation imaging to the execution of radiation imaging performed by the imaging control apparatus 101, the first radiation imaging apparatus 102, and the second radiation imaging apparatus 103 is similar to that in the first embodiment (FIGS. 3A and 3B).

Operations in steps S201 and S202 are similar to those in the first embodiment (FIG. 4). In step S1201, the information correcting unit 1018 of the imaging control apparatus 101 corrects the average pixel values acquired from a plurality of radiation imaging apparatuses based on characteristic information stored in the characteristic information storage unit 1017. For example, the information correcting unit 1018 corrects the average pixel values into those when the respective radiation imaging apparatuses are matched with a predetermined sensitivity as a reference by using sensitivity information of the radiation imaging apparatuses.

In step S1202, the imaging control apparatus 101 (the selecting unit 1013) compares the average pixel values corrected in step S1201 to select a radiation imaging apparatus that has provided the largest average pixel value. Although the above description has exemplified the arrangement configured to select a radiation imaging apparatus that has provided the largest average pixel value, this is not exhaustive. For example, various modifications can be made as described with reference to step S203 in the first embodiment. Subsequently, in step S1203, the imaging control apparatus 101 (an image acquiring unit 1014) acquires a radiation image from the radiation imaging apparatus (the first radiation imaging apparatus 102 in this case) selected in step S1202. That is, the imaging control apparatus 101 requests the first radiation imaging apparatus 102 to transmit an image. In accordance with the request for an image from the imaging control apparatus 101, a transmitting unit 1023 of the first radiation imaging apparatus 102 transmits a radiation image to the imaging control apparatus 101.

As described above, according to the seventh embodiment, the system that executes radiation imaging while a plurality of radiation imaging apparatuses are set in the imaging enabled state corrects the imaging information acquired from a plurality of radiation imaging apparatuses based on characteristic information of the respective radiation imaging apparatuses. The imaging control apparatus 101 can equally compare imaging information of a plurality of radiation imaging apparatuses by referring to corrected imaging information. This reduces the chance of acquiring a radiation image without any object image due to erroneous selection of a radiation imaging apparatus.

Eighth Embodiment

In the seventh embodiment, the information correcting unit 1018 in the imaging control apparatus 101 corrects the imaging information acquired by the information acquiring unit 1012 based on characteristic information of a plurality of radiation imaging apparatuses, and the selecting unit 1013 selects a radiation imaging apparatus based on the corrected imaging information. The eighth embodiment will exemplify an arrangement in which a first radiation imaging apparatus 102 and a second radiation imaging apparatus 103 correct imaging information by using characteristic information and provide the corrected imaging information to an imaging control apparatus 101.

Figure 13:
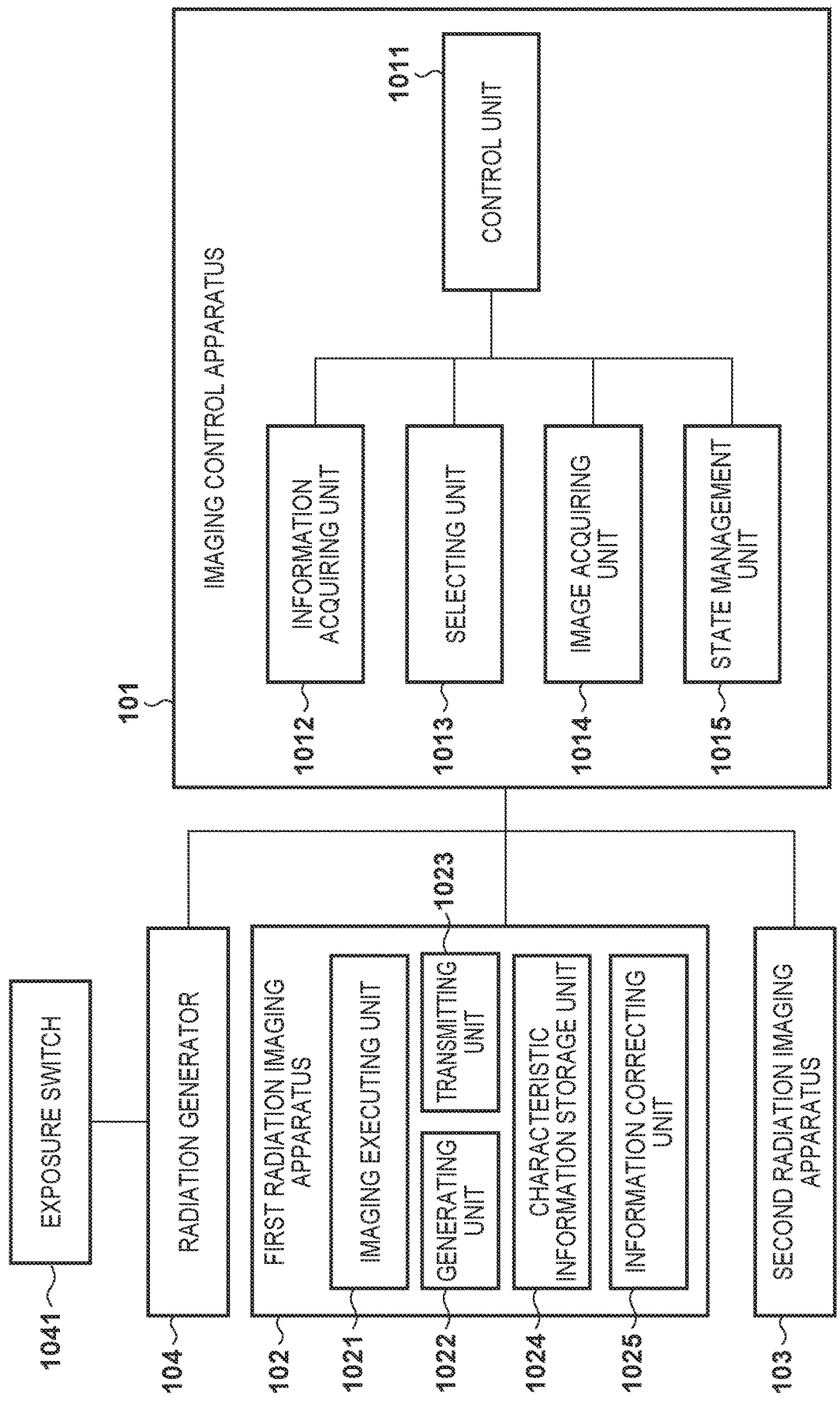
FIG. 13 is a block diagram showing an example of the functional arrangement of a radiation imaging system according to the eighth embodiment.

FIG. 13 is a block diagram showing an example of the functional arrangement of a radiation imaging system according to the eighth embodiment. The same reference numerals denote similar components to those in the first embodiment (FIG. 1). Note that the hardware arrangement of a radiation imaging system according to the eighth embodiment is similar to that of the first embodiment (FIG. 2). In the eighth embodiment, the first radiation imaging apparatus 102 additionally includes a characteristic information storage unit 1024 and an information correcting unit 1025. The characteristic information storage unit 1024 has a similar function to that of the characteristic information storage unit 1017 according to the seventh embodiment. The information correcting unit 1025 has the same function as that of the information correcting unit 1018 according to the seventh embodiment. That is, each of a plurality of radiation imaging apparatuses according to the eighth embodiment includes the characteristic information storage unit 1024 storing characteristic information representing characteristics of the radiation imaging apparatus. In addition, each of a plurality of radiation imaging apparatuses according to the eighth embodiment includes the information correcting unit 1025 that corrects the imaging information generated by a generating unit 1022 based on characteristic information stored in the characteristic information storage unit 1024.

Figure 14:
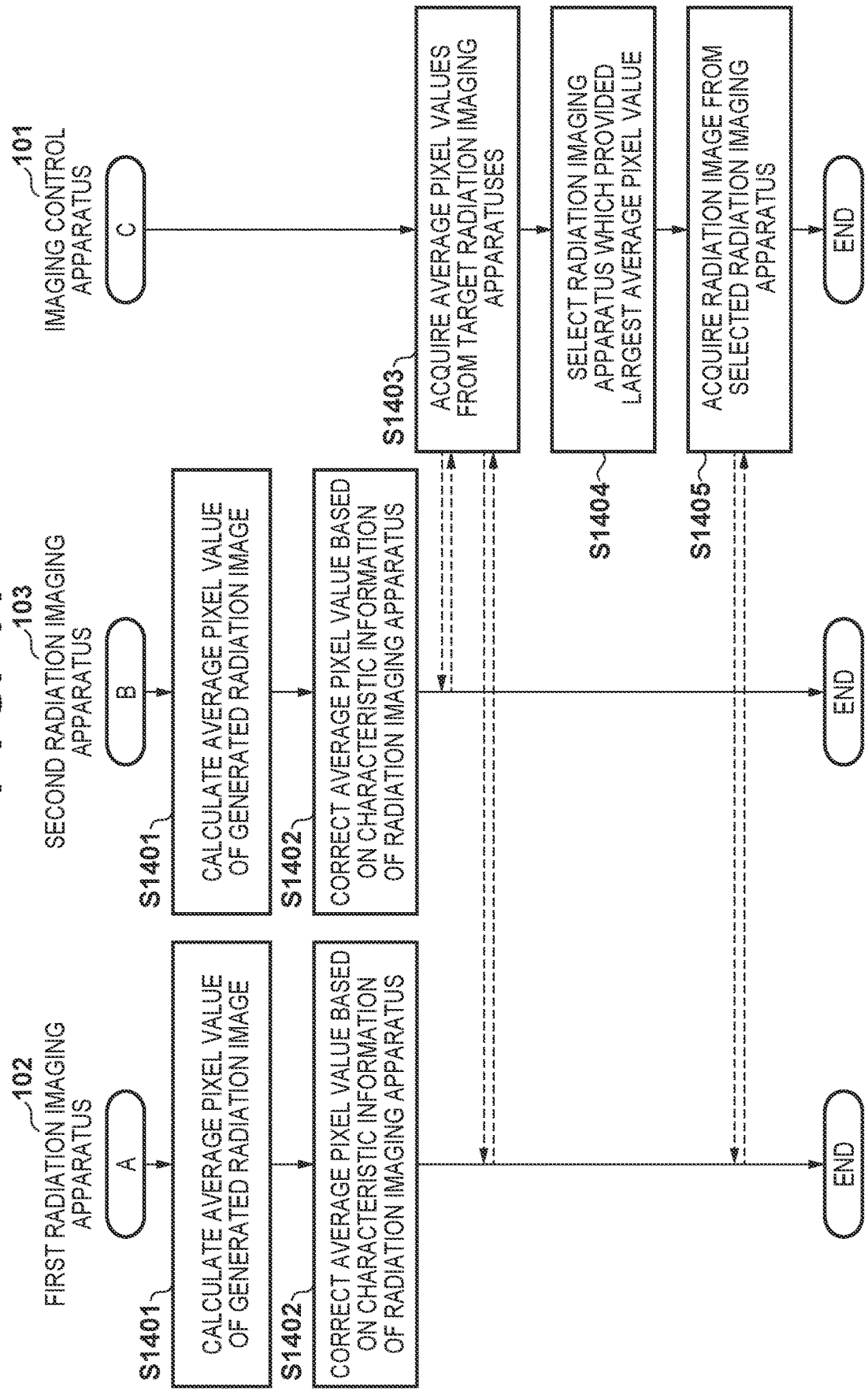
FIG. 14 is a flowchart showing a radiation image acquiring operation according to the eighth embodiment.

FIG. 14 is a flowchart showing an example of an operation from the execution of radiation imaging by the first radiation imaging apparatus 102 and the second radiation imaging apparatus 103 to the acquisition of a radiation image by the imaging control apparatus 101. Note that an operation from preparation for radiation imaging to the execution of radiation imaging in the eighth embodiment is similar to that in the first embodiment (FIGS. 3A and 3B).

Referring to FIG. 14, in step S1401, the generating unit 1022 of each of the first radiation imaging apparatus 102 and the second radiation imaging apparatus 103 calculates statistic information of pixel values of the generated radiation image as imaging information. Step S1401 is similar to step S201 in the first embodiment. In step S1402, the information correcting unit 1025 corrects the average pixel value calculated by each radiation imaging apparatus based on characteristic information stored in the characteristic information storage unit 1024. The correction method is similar to that in the seventh embodiment. A transmitting unit 1023 transmits the imaging information corrected by the information correcting unit 1025 to the imaging control apparatus 101.

In step S1403, the imaging control apparatus 101 (the information acquiring unit 1012) acquires the corrected average pixel values from the first radiation imaging apparatus 102 and the second radiation imaging apparatus 103. In step S1404, the imaging control apparatus 101 (the selecting unit 1013) compares the corrected average pixel values acquired in step S1403 to select a radiation imaging apparatus that has provided the largest average pixel value. Processing in steps S1403 and S1404 is similar to that in steps S202 and S203 in the first embodiment (FIG. 4) except that average pixel values after correction are used. As described with reference to step S203, therefore, it is possible to use selection of a radiation imaging apparatus based on various types of imaging information. Note, however, that imaging information to be used is information corrected by each radiation imaging apparatus.

Subsequently, in step S1405, the imaging control apparatus 101 (the image acquiring unit 1014) acquires a radiation image from the radiation imaging apparatus (the first radiation imaging apparatus 102 in this case) selected in step S1404. Processing in step S1405 is similar to that in step S204.

As described above, according to the eighth embodiment, the imaging control apparatus 101 acquires the imaging information corrected based on characteristic information obtained based on a predetermined reference from each of a plurality of radiation imaging apparatuses, and selects a radiation imaging apparatus by using the corrected imaging information. By using the corrected imaging information, the imaging information from a plurality of radiation imaging apparatuses is equally compared. This reduces the chance of acquiring a radiation image without any object image due to erroneous selection of a radiation imaging apparatus.

Although the seventh and eighth embodiments are described based on the arrangement according to the first embodiment, this is not exhaustive. Obviously, the correction of imaging information and the selection of a radiation imaging apparatus based on the corrected imaging information according to the seventh and eighth embodiments can be applied to the imaging information acquired in the second to sixth embodiments.

Modification

The seventh and eighth embodiments each have exemplified the case in which an average pixel value as imaging information is corrected by using sensitivity information as characteristic information. However, characteristic information that can be used for the correction of imaging information is not limited to sensitivity information.

For example, effective pixel information enabling radiation detection and ineffective pixel information (defective pixel information) disabling radiation detection may be used as characteristic information. That is, characteristic information may include defective pixel information representing a pixel incapable of detecting radiation from an imaging apparatus so as to allow the information correcting unit 1018 and the information correcting unit 1025 to correct imaging information by using the defective pixel information. In this case, for example, an average pixel value may be corrected based on the ratio of the number of effective pixels to the total number of pixels obtained from effective pixel information and ineffective pixel information.

Alternatively, dark correction information (or a dark image) obtained by performing an imaging operation without irradiating a radiation imaging apparatus with radiation may be used as characteristic information. That is, characteristic information includes the dark image acquired by performing an imaging operation without irradiating a radiation imaging apparatus with radiation. The information correcting unit 1018 or the information correcting unit 1025 corrects imaging information by using the dark image. In this case, for example, an average pixel value may be corrected by using the average value of pixels calculated from dark correction information or a dark image. Note that because a dark image is obtained accompanying an imaging operation, the information correcting unit 1025 of the radiation imaging apparatus preferably executes correction of imaging information using a dark image.

Alternatively, the type of phosphor of a radiation imaging apparatus may be used as characteristic information. The type of phosphor is associated with the sensitivity of the radiation imaging apparatus. In this case, the characteristic information includes the type information of the phosphor of the radiation imaging apparatus, and the information correcting unit 1018 or the information correcting unit 1025 corrects imaging information by using the type information of the phosphor. When the information correcting unit 1018 of the imaging control apparatus 101 performs correction, the imaging information transmitted from the radiation imaging apparatus includes an average pixel value and the type information of the phosphor. Note that when the type of phosphor can be identified by the model number of a radiation imaging apparatus, the model number of the radiation imaging apparatus may be used as type information of the phosphor.

In the above embodiment, sensitivity information of radiation imaging apparatuses is used to correct the average pixel value obtained from each radiation imaging apparatus into an average pixel value when the radiation imaging apparatus is matched with a predetermined sensitivity as a reference. However, this is not exhaustive. For example, a reference radiation imaging apparatus may be determined among a plurality of radiation imaging apparatuses, and the average pixel values obtained from the remaining radiation imaging apparatuses may be corrected in accordance with sensitivity information of the reference radiation imaging apparatus.

The above characteristic information (for example, sensitivity information) may include correction information (sensitivity correction information) for correcting the characteristic information, such as an imaging environment (for example, an ambient temperature and the temperature of a radiation imaging apparatus itself) and deterioration information based on temporal changes. The information correcting unit 1018 or the information correcting unit 1025 may correct characteristic information (for example, sensitivity information) by using correction information (for example, sensitivity correction information) representing a change in characteristic information and correct imaging information (for example, an average pixel value) by using the corrected characteristic information. In addition, temporal change information (a time-related function) set in advance for each of a plurality of radiation imaging apparatuses may be held as correction information, and the information correcting unit 1018 or the information correcting unit 1025 may correct characteristic information based on the operation time of a corresponding one of the radiation imaging apparatuses. This makes it possible to give consideration to a change in characteristic information due to a temporal change.

Note that characteristic information of each radiation imaging apparatus is not limited to the information described above and may be combination of a plurality of pieces of characteristic information. That is, an imaging information correction method is not limited to the above method, and a plurality of correction methods may be combined.

Ninth Embodiment

Figure 15:
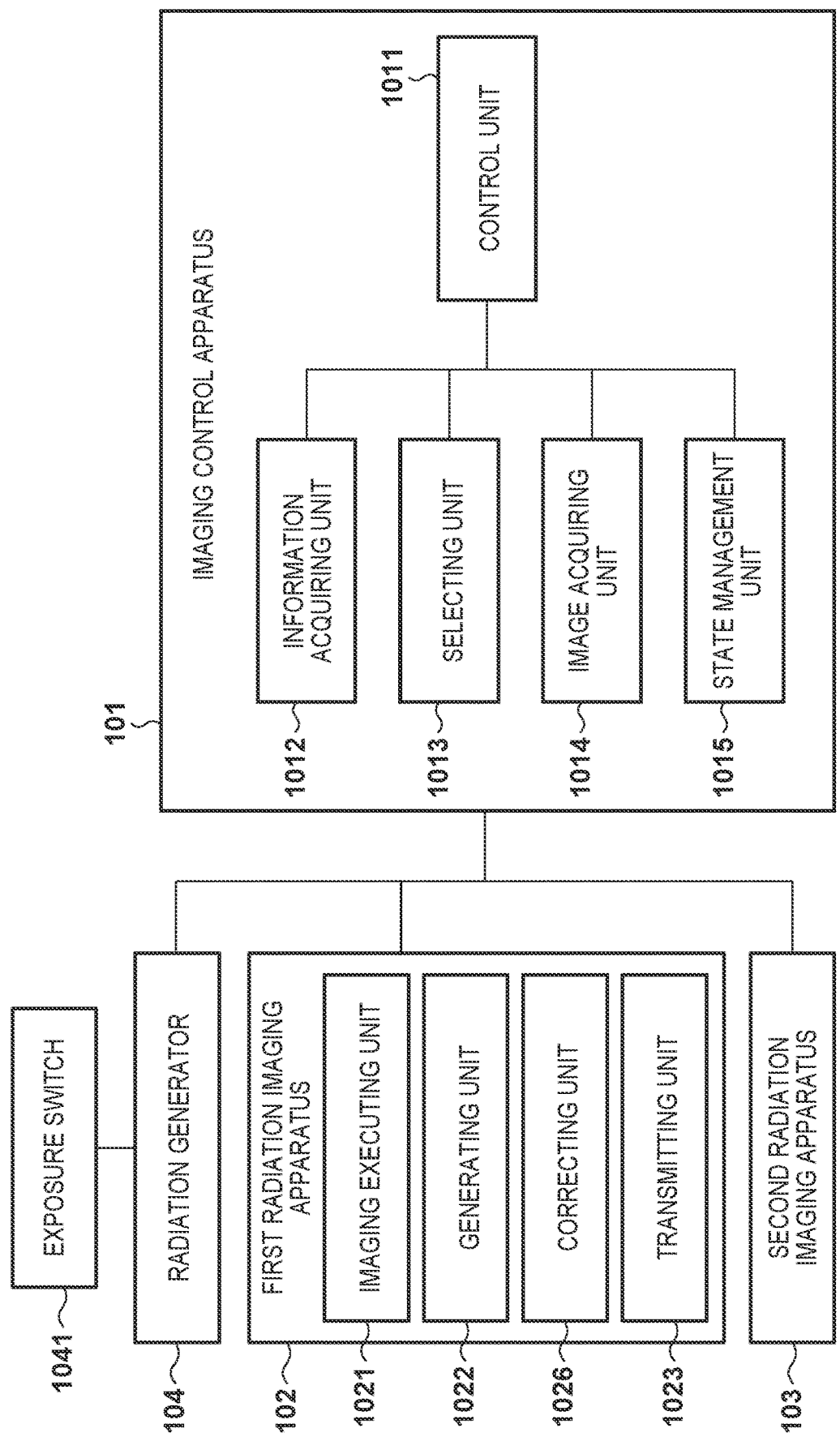
FIG. 15 is a block diagram showing an example of the functional arrangement of a radiation imaging system according to the ninth embodiment.

FIG. 15 shows an example of the arrangement of a radiation imaging system according to the ninth embodiment. The same reference numerals denote similar components to those in the first embodiment (FIG. 1). Note that the hardware arrangement of a radiation imaging system according to the ninth embodiment is similar to that of the first embodiment (FIG. 2). In the ninth embodiment, a first radiation imaging apparatus 102 and a second radiation imaging apparatus 103 additionally include correcting units 1026.

In the first radiation imaging apparatus 102, an imaging executing unit 1021 acquires a radiation image by executing a first imaging operation at the time of irradiation with radiation. In addition, the imaging executing unit 1021 obtains a dark image (dark output) by executing a second imaging operation without irradiation of radiation. Based on the radiation image obtained by the first imaging operation, a generating unit 1022 generates imaging information with a smaller data size than the radiation image. In this embodiment, the average value of pixel values of a radiation image is used as imaging information. The correcting unit 1026 acquires a dark image by the second imaging operation, and generates a corrected image by correcting (first image correction) the radiation image acquired by the first imaging operation with the dark image. The second imaging operation is executed following the first imaging operation. A transmitting unit 1023 transmits the imaging information generated by the generating unit 1022 to an external apparatus (an imaging control apparatus 101 in this embodiment). The transmitting unit 1023 transmits the corrected image generated by the correcting unit 1026 to an external apparatus (the imaging control apparatus 101) in accordance with a request from the external apparatus. The second radiation imaging apparatus 103 has a similar functional arrangement to that described above.

FIGS. 16A and 16B are flowcharts showing an example of an operation according to the ninth embodiment, from preparation for radiation imaging to the execution of radiation imaging, performed by the imaging control apparatus 101, the first radiation imaging apparatus 102, and the second radiation imaging apparatus 103. Operations from step S101 to step S104 are similar to those in the first embodiment (FIGS. 3A and 3B).

In step S1605, the generating unit 1022 of each of the first radiation imaging apparatus 102 and the second radiation imaging apparatus 103 calculates, as imaging information, statistic information calculated based on the pixel values of the radiation image obtained by radiation imaging. The ninth embodiment uses the average value of pixel values (to be referred to as an average pixel value hereinafter) of a radiation image as statistic information. In step S1606, the first radiation imaging apparatus 102 and the second radiation imaging apparatus 103 notify the imaging control apparatus 101 of the termination of imaging.

Note that the ninth embodiment uses an average pixel value as statistic information. However, this is not exhaustive. For example, statistic information such as the maximum value, median value, or variance value of pixel values may be used. Alternatively, it is possible to use statistic information such as the maximum value of the differences between the pixel values of adjacent pixels or the width between the maximum value and the minimum values of pixel values. Note that pixel values may be luminance values or density values. In addition, two or more pieces of statistic information may be calculated.

A calculation range for statistic information need not be an entire radiation image as described in the third, fifth, and sixth embodiments. That is, statistic information as imaging information may be calculated by using the pixel values of an image (pixel group) that is generated based on a radiation image and having a smaller data size than the radiation image. For example, pixels in a region of interest or irradiation field detected from a radiation image may be used as information from which statistic information is obtained, or a thinned-out image or reduced image deriving from a radiation image may be used as information from which statistic information is obtained. Alternatively, pixels at one or more coordinates determined in advance in a radiation image may be used as information from which statistic information is obtained. Note that a reduced image is generated by, for example, calculating the pixel value of one pixel (for example, calculating the average value of neighboring pixels) from the pixel values of a plurality of pixels. In addition, a region of interest is detected by analyzing a radiation image using a known method. Furthermore, an irradiation field may be detected by analyzing a radiation image or determined based on information (information concerning a collimator) concerning irradiation conditions of a radiation generator 104 acquired from the imaging control apparatus 101.

According to the above description, the generating unit 1022 generates statistic information as imaging information. However, this is not exhaustive. For example, as described in the fourth embodiment, the generating unit 1022 may generate an image based on a radiation image and having a smaller data size than the radiation image, and an information acquiring unit 1012 may acquire the generated image as imaging information. A selecting unit 1013 generates predetermined statistic information (for example, an average pixel value) from the acquired imaging information (an image with a small data size), and selects one radiation imaging apparatus based on the generated statistic information. In this case as well, it is possible to use, as an image provided as imaging information, a thinned-out image, a reduced image, a region of interest, an irradiation field, pixels at preset coordinates, and the like.

FIG. 17 is a flowchart showing an example of an operation according to the first embodiment, from the execution of radiation imaging to the acquisition of a radiation image, performed by the imaging control apparatus 101, the first radiation imaging apparatus 102, and the second radiation imaging apparatus 103.

In step S1701, the imaging control apparatus 101 (the information acquiring unit 1012) acquires the average pixel value calculated in step S1605 from each of the first radiation imaging apparatus 102 and the second radiation imaging apparatus 103 via the transmitting unit 1023. In step S1702, the selecting unit 1013 compares the average pixel values acquired in step S1701 to select a radiation imaging apparatus that has provided the largest average pixel value. Although the ninth embodiment is configured to select a radiation imaging apparatus that has provided the largest average pixel value, this is not exhaustive. For example, a radiation imaging apparatus that has provided statistic information nearest to a preset threshold may be selected or a radiation imaging apparatus may be selected by comparing a plurality of pieces of statistic information. In addition, when a comparison result indicates no difference and hence does not allow selection of one radiation imaging apparatus, any radiation imaging apparatus that has notified first the execution of radiation imaging may be selected.

In step S1704, the correcting unit 1026 of each of the first radiation imaging apparatus 102 and the second radiation imaging apparatus 103 acquires a dark image by executing imaging under the same imaging conditions as those for radiation imaging in step S104 without irradiation of radiation. The correcting unit 1026 subtracts the dark image acquired in step S1704 from the radiation image acquired in step S104 to obtain a corrected radiation image. In step S1705, the first radiation imaging apparatus 102 and the second radiation imaging apparatus 103 each notify the imaging control apparatus 101 of the termination of the above correction.

Upon reception of the notification of the termination of correction in step S1705, the imaging control apparatus 101 (an image acquiring unit 1014) acquires, in step S1703, a corrected radiation image from the radiation imaging apparatus (the first radiation imaging apparatus 102 in this case) selected in step S1702.

According to the flowcharts in FIGS. 16A, 16B, and 17, the processing of acquiring and correcting a dark image (step S1704) in the radiation imaging apparatus is executed concurrently with the processing of selecting a radiation imaging apparatus by the imaging control apparatus 101 (step S1702). However, this is not exhaustive. For example, the processing of generating and notifying imaging information after the acquisition of a radiation image (steps S1605 and S1606) in a radiation imaging apparatus can be executed concurrently, at least partly, with the processing of generating and notifying a corrected image from the acquisition of a dark image (steps S1704 and S1705). This can make a first period from the start of the generation of imaging information by the generating unit 1022 to the selection of a radiation imaging apparatus by the selecting unit 1013 at least partly overlap a second period during which the correcting unit 1026 acquires a dark image and generates a corrected image. This makes it possible to shorten the imaging cycle.

FIG. 21 shows this state. In the radiation imaging apparatus, the imaging executing unit 1021 executes a first imaging operation (an accumulating operation 2101 and a readout operation 2102 in a radiation detection panel 51) in synchronism with irradiation with radiation from the radiation generator 104 (steps S104 and S1605). In addition, the imaging executing unit 1021 executes a second imaging operation (an accumulating operation 2103 and a readout operation 2104 in the radiation detection panel 51 without irradiation of radiation) for obtaining a dark image following the first imaging operation (step S1704). The correcting unit 1026 obtains a corrected image by correcting the radiation image obtained by the first imaging operation by using the dark image obtained by the second imaging operation (correction processing 2106). The second imaging operation by the imaging executing unit 1021 and the period of the correction processing 2106 correspond to the above second period (steps S1704 and S1705). The generating unit 1022 performs imaging information generation 2105 from the radiation image independently of the second imaging operation and the correction processing 2106, and the transmitting unit 1023 transmits the imaging information to the imaging control apparatus 101. In the imaging control apparatus 101, the information acquiring unit 1012 sequentially acquires imaging information from the first radiation imaging apparatus 102 and the second radiation imaging apparatus 103 (steps 2121 and 2122), and the selecting unit 1013 selects a radiation imaging apparatus based on the acquired imaging information (step 2123). The period from the start of the generation of imaging information by the generating unit 1022 to the selection of a radiation imaging apparatus by the selecting unit 1013 corresponds to the above first period (steps S1605, S1606, S1701, and S1702).

As described above, according to the ninth embodiment, the period during which the information acquiring unit 1012 and the selecting unit 1013 acquire imaging information from a plurality of radiation imaging apparatuses and select a radiation imaging apparatus partially overlaps the period during which the correcting unit 1026 acquires a dark image and generates a corrected image. It is possible to shorten the imaging cycle of the radiation imaging system by executing the processing for selecting a radiation imaging apparatus (generation and selection of imaging information) concurrently with the processing of acquiring and correcting a dark image.

Note that if there are many radiation imaging apparatuses, selection of a radiation imaging apparatus in step S1702 may delay with respect to notification of the termination of correction in step S1705. Obviously, however, this can shorten the imaging cycle compared with starting acquisition of imaging information (an average pixel value) and selection of a radiation imaging apparatus (steps S1701 and S1702) after waiting for the notification of the termination of correction in step S1705.

Tenth Embodiment

FIG. 18 is a block diagram showing an example of the arrangement of a radiation imaging system according to the 10th embodiment. The same reference numerals denote similar components to those in the ninth embodiment (FIG. 15). The hardware arrangement of the radiation imaging system according to the 10th embodiment is similar to that of the first embodiment (FIG. 2). An imaging control apparatus 101 according to the 10th embodiment includes a characteristic correcting unit 1116 that corrects a radiation image (second image correction) by using characteristic correction information corresponding to each of a plurality of radiation imaging apparatuses, a memory unit 1117 that allows fast access, and a storage unit 1118 that holds data in a nonvolatile manner. Note that the memory unit 1117 is formed by using, for example, a RAM 13, and the storage unit 1118 is formed by using a secondary memory device 14. The storage unit 1118 stores characteristic correction information of each of a plurality of radiation imaging apparatuses.

The characteristic correcting unit 1116 can perform fast characteristic correction by deploying information for characteristic correction from the storage unit 1118 that can record in a nonvolatile manner, typified by an HDD, to the memory unit 1117 that allows fast access. Note that characteristics that the characteristic correcting unit 1116 corrects are, for example, characteristics of the radiation imaging apparatus such as variation in gain of the radiation detection panel 51 and pixel defects. Gain correction is performed to correct variations in gain by using the image obtained by imaging while reference light enters the photoelectric conversion element of the radiation detection panel 51 as a gain correction image. When performing gain correction, the characteristic correcting unit 1116 acquires the gain correction image obtained in advance by imaging from the storage unit 1118 and uses the image upon deploying it in the memory unit 1117. For example, when performing defect correction, the characteristic correcting unit 1116 acquires defect information for defect correction obtained in advance by imaging from the storage unit 1118 and uses the information upon deploying it in the memory unit 1117.

FIGS. 19A and 19B are flowcharts showing an example of an operation according to the 10th embodiment, from preparation for radiation imaging to the execution of radiation imaging, performed by the imaging control apparatus 101, the first radiation imaging apparatus 102, and the second radiation imaging apparatus 103.

In step S101, the first radiation imaging apparatus 102 and the second radiation imaging apparatus 103 are set in the standby state. In the standby state, the first radiation imaging apparatus 102 and the second radiation imaging apparatus 103 establish communication with the imaging control apparatus 101. In step S1901, the characteristic correcting unit 1116 deploys characteristic correction information (a gain correction image or defect information) for all usable radiation imaging apparatuses from the storage unit 1118 to the memory unit 1117. That is, before the imaging operations of a plurality of radiation imaging apparatuses, the characteristic correcting unit 1116 causes the memory unit 1117 that allows faster access than the storage unit 1118 to hold characteristic correction information for a plurality of radiation imaging apparatuses stored in the storage unit 1118. According to the 10th embodiment, characteristic correction information corresponding to the first radiation imaging apparatus 102 and the second radiation imaging apparatus 103 is deployed in the memory unit 1117. Processing in and after step S102 is similar to that in the ninth embodiment (FIGS. 16A and 16B).

FIGS. 20A and 20B are flowcharts showing an example of an operation according to the 10th embodiment, from the execution of radiation imaging to the acquisition of a radiation image and the correction of characteristics, performed by the imaging control apparatus 101, the first radiation imaging apparatus 102, and the second radiation imaging apparatus 103. Processing in steps S1701 to S1705 is similar to that in the 10th embodiment (FIG. 17).

After step S1703, the characteristic correcting unit 1116 reads out characteristic correction information of the radiation imaging apparatus selected by the selecting unit 1013 from the memory unit 1117 and corrects the image acquired by an image acquiring unit 1014. That is, in step S2001, the characteristic correcting unit 1116 acquires characteristic correction information of the radiation imaging apparatus (the first radiation imaging apparatus in this case) selected in step S1702 from the characteristic correction information deployed in advance in the memory unit 1117 in step S1901. The characteristic correcting unit 1116 corrects the radiation image acquired in step S1703 by using the acquired characteristic correction information.

Assume that characteristic correction information of all the radiation imaging apparatuses has not entirely deployed from the storage unit 1118 to the memory unit 1117 in step S1901. In this case, it is necessary to add the step of deploying characteristic correction information of the radiation imaging apparatus selected in step S1702 from the storage unit 1118 to the memory unit 1117 before the execution of step S2001. This prolongs the radiation imaging cycle.

As described above, according to the 10th embodiment, when executing characteristic correction for a radiation imaging apparatus, the imaging control apparatus 101 deploys characteristic correction information of all the radiation imaging apparatuses in a fast-access memory before imaging. This makes it possible to execute characteristic correction processing after image acquisition at high speed, thereby shortening the radiation imaging cycle.

Note that the arrangements and control operations of the first to 10th embodiments described above can be combined as needed.

According to the present invention, a radiation imaging system including a plurality of usable radiation imaging apparatuses can perform radiation imaging in a short cycle.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging system comprising:
a plurality of imaging apparatuses configured to generate images based on radiation emitted from a radiation generator; and
a control apparatus configured to communicate with the plurality of imaging apparatuses,
wherein each of the plurality of imaging apparatuses is configured to generate imaging information with a smaller data size than an image obtained by an imaging operation based on the image, and
the control apparatus includes:
one or more processors; and
a memory including instructions stored thereon that, when executed by the one or more processors, cause the control apparatus to function as:
an information acquiring unit configured to acquire the imaging information from each of the plurality of imaging apparatuses; and
a selecting unit configured to select, from the plurality of imaging apparatuses, an imaging apparatus from which an image obtained by an imaging operation is acquired, based on the imaging information acquired by the information acquiring unit.

2. The radiation imaging system according to claim 1, wherein the instructions, when executed by the one or more processors, further cause the control apparatus to function as an image acquiring unit configured to acquire an image from an imaging apparatus selected by the selecting unit.

3. The radiation imaging system according to claim 2, wherein the instructions, when executed by the one or more processors, further cause the control apparatus to function as a re-acquisition instructing unit configured to issue an instruction to acquire, after acquisition of an image from the imaging apparatus selected by the selecting unit, an image from another imaging apparatus, and
the image acquiring unit acquires an image from the other imaging apparatus in accordance with an instruction from the re-acquisition instructing unit.

4. The radiation imaging system according to claim 2, wherein the instructions, when executed by the one or more processors, further cause the control apparatus to function as a first image correcting unit configured to acquire a dark image by an imaging operation without irradiation of radiation and generate a corrected image by correcting the image with the dark image, and
wherein the image acquiring unit acquires the corrected image from the imaging apparatus selected by the selecting unit.

5. The radiation imaging system according to claim 4, wherein a first period from a start of generation of the imaging information to selection of an imaging apparatus by the selecting unit overlaps, at least partly, a second period from acquisition of the dark image by the first image correcting unit to generation of a corrected image.

6. The radiation imaging system according to claim 4, wherein the instructions, when executed by the one or more processors, further cause the control apparatus to function as:
a storage unit configured to store characteristic correction information concerning each of the plurality of imaging apparatuses;
a holding unit configured to cause a memory that allows faster access than the storage unit to hold characteristic correction information of the plurality of imaging apparatuses stored in the storage unit before imaging operations of the plurality of imaging apparatuses; and
a second image correcting unit configured to correct an image acquired by the image acquiring unit by reading out characteristic correction information of the imaging apparatus selected by the selecting unit from the memory.

7. The radiation imaging system according to claim 1, wherein statistic information of pixel values of the image is generated by each of the plurality of imaging apparatuses as the imaging information.

8. The radiation imaging system according to claim 7, wherein the statistic information is generated by each of the plurality of imaging apparatuses by using an image generated based on the image and having a smaller data size than the image.

9. The radiation imaging system according to claim 8, wherein the image with the smaller data size is any one of a thinned-out image of the image, a reduced image, an image constituted by pixels at predetermined coordinates, an image in a region of interest, and an image in an irradiation field.

10. The radiation imaging system according to claim 7, wherein the statistic information is any one of an average value of pixel values, a maximum value of pixel values, a median value of pixel values, a variance value of pixel values, a maximum value of differences in pixel value between adjacent pixels, and a width between a maximum value and a minimum value of pixel values.

11. The radiation imaging system according to claim 1, wherein, as the imaging information, an image with a smaller data size than the image is generated by each of the plurality of imaging apparatuses based on the image, and
the selecting unit generates predetermined statistic information from pixel values of the image with a small data size and selects an imaging apparatus based on the generated statistic information.

12. The radiation imaging system according to claim 1, wherein the instructions, when executed by the one or more processors, further cause the control apparatus to function as:
a storage unit configured to store characteristic information representing a characteristic of each of the plurality of imaging apparatuses; and
an information correcting unit configured to correct the imaging information acquired from the plurality of imaging apparatuses based on the characteristic information stored in the storage unit.

13. The radiation imaging system according to claim 12, wherein the storage unit includes a storage unit configured to store characteristic information representing a characteristic of each of the plurality of imaging apparatuses in each of the plurality of imaging apparatuses.

14. The radiation imaging system according to claim 12, wherein the storage unit includes a storage unit configured to store characteristic information representing characteristics of the plurality of imaging apparatuses in the control apparatus.

15. The radiation imaging system according to claim 12, wherein the information correcting unit corrects, based on the characteristic information, the imaging information into image information for a state in which a sensitivity of each of the plurality of imaging apparatuses is matched with a reference sensitivity.

16. The radiation imaging system according to claim 15, wherein a sensitivity as the reference is a sensitivity of one imaging apparatus of the plurality of imaging apparatuses.

17. The radiation imaging system according to claim 12, wherein the characteristic information includes defective pixel information representing a pixel that is not configured to detect radiation in the imaging apparatus, and the information correcting unit corrects the imaging information by using the defective pixel information.

18. The radiation imaging system according to claim 12, wherein the characteristic information includes a dark image acquired by performing an imaging operation without irradiating the imaging apparatus with radiation, and the information correcting unit corrects the imaging information by using the dark image.

19. The radiation imaging system according to claim 12, wherein the characteristic information includes type information of a phosphor of the imaging apparatus, and the information correcting unit corrects the imaging information by using the type information of the phosphor.

20. The radiation imaging system according to claim 12, wherein the characteristic information is corrected based on a temporal change determined in advance for each of the plurality of imaging apparatuses and an operation time of each of the imaging apparatuses.

21. A control apparatus that is configured to communicate with a plurality of imaging apparatuses that generate images based on radiation emitted from a radiation generator, comprising:
one or more processors; and
a memory including instructions stored thereon that, when executed by the one or more processors, cause the control apparatus to function as:
an information acquiring unit configured to acquire imaging information generated based on an image obtained by an imaging operation and having a smaller data size than the image from each of the plurality of imaging apparatuses;
a selecting unit configured to select one imaging apparatus from the plurality of imaging apparatuses based on the imaging information acquired by the information acquiring unit; and
an image acquiring unit configured to acquire an image from the imaging apparatus selected by the selecting unit.

22. A method of controlling a radiation imaging system including a plurality of imaging apparatuses configured to generate images based on radiation emitted from a radiation generator, and a control apparatus configured to communicate with the plurality of imaging apparatuses, the method comprising:
causing each of the plurality of imaging apparatuses to generate imaging information with a smaller data size than an image obtained by an imaging operation based on the image;
causing the control apparatus to acquire the imaging information from each of the plurality of imaging apparatuses; and
a selecting step of causing the control apparatus to select, from the plurality of imaging apparatuses, an imaging apparatus from which an image obtained by an imaging operation is acquired based on the acquired imaging information.

23. A non-transitory computer-readable storage medium storing a computer program for causing a compute to execute the method according to claim 22.

24. A method of controlling a control apparatus that is configured to communicate with a plurality of imaging apparatuses that generate images based on radiation emitted from a radiation generator, the method comprising:
   acquiring imaging information generated based on an image obtained by an imaging operation and having a smaller data size than the image from each of the plurality of imaging apparatuses;
   selecting one imaging apparatus from the plurality of imaging apparatuses based on the acquired imaging information; and
   acquiring an image from the selected one imaging apparatus.

25. A non-transitory computer-readable storage medium storing a computer program for causing a compute to execute the method according to claim 24.

* * * * *